US006444802B1

(12) United States Patent
Kapeller-Libermann et al.

(10) Patent No.: US 6,444,802 B1
(45) Date of Patent: Sep. 3, 2002

(54) HUMAN AMINOPEPTIDASE

(75) Inventors: Rosana Kapeller-Libermann, Chestnut Hill; David White, Braintree; Immaculada Silos-Santiago, Cambridge, all of MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/409,180

(22) Filed: Sep. 30, 1999

(51) Int. Cl.[7] .................. C07H 21/04; C07H 21/02; C12P 21/06; C12N 15/00; G01N 33/53

(52) U.S. Cl. .................. 536/23.2; 536/23.1; 435/69.1; 435/320.1; 435/325; 435/810; 435/975

(58) Field of Search .................. 536/23.1, 23.2; 435/69.1, 320.1, 325, 810, 975

(56) References Cited

PUBLICATIONS

Dauch et al., "Molecular Cloning and Expression of Rat Brain Endopeptidase 3.4.24.16," *The Journal of Biological Chemistry*, Nov. 10, 1995, pp. 27266–27271, vol. 270, No. 45.

Kawabata et al., "Rabbit Liver Microsomal Endopeptidase with Substrate Specificity for Processing Proproteins Is Structurally Related to Rat Testes Metalloendopeptidase 24.15," *The Journal of Biological Chemistry*, Jun. 14, 1993, pp. 12498–12503, vol. 268, No. 17.

Krause et al., "Characterization and Localization of Mitochondrial Oligopeptidase (MOP) (EC 3.4.24.16) Activity in the Human Cervical Adenocarcinoma Cell Line HeLa," *Journal of Cellular Biochemistry*, 1997, pp. 297–308, vol. 66, No. 3.

Nagase et al., "Prediction of the Coding Sequences of Unidentified Human Genes. XV. The Complete Sequences of 100 new cDNA Clones from Brain Which Code for Large Proteins in vitro," *DNA Research*, 1999, pp. 337–345, vol. 6.

NCI–CGAP, National Cancer Institute, Cancer Genome Anatomy Project (CGAP), Tumor Gene Index, Sep. 9, 1999, Unpublished, EMBL Accession No. AW003054.

Sugiura et al., "Molecular Cloning of Porcine Soluble Angiotensin–binding Protein," *The Journal of Biological ChemistryI*, Sep. 5, 1992, pp. 18067–18072, vol. 267, No. 25.

Vincent et al., "Purification and Characterization of Human Endopeptidase 3.4.24.16. Comparison with the Porcine Indicates a Unique Cleavage Site on Neurotensin," *Brain Research*, 1996, pp. 51–58, vol. 709, No. 1.

Serizawa et al., Characterization of a Mitochondrail Metallopeptidase Reveals Neurolysin as a Homologue of Thimet Oligopeptidase, Journal of Applied Physiology, Online, Feb. 3, 1995, pp. 2092–2098, vol. 270, No. 5, The American Society for Biochemistry and Molecular Biology, Inc.

National Cancer Institute, Cancer Genome Anatomy Project, 1997, Unpublished; GenBank Accession No. AI952756, Created Aug. 19, 1999, Last Updated Mar. 8, 2000.

National Cancer Institute, Cancer Genome Anatomy Project, 1997, Unpublished; GenBank Accession No. AI214321, Created Oct. 21, 1998, Last Updated Feb. 3, 1999.

Marra et al., The WashU–HHMI Mouse EST Project, 1996, Unpublished; GenBank Accession No. AI326417, Created Dec. 23, 1998, Last Updated Dec. 23, 1998.

National Cancer Institute, Cancer Genome Anatomy Project, 1997, Unpublished; GenBank Accession No. AI379544, Created Jan. 25, 1999; Last Updated Mar. 18, 1999.

Hillier et al., The WashU–Merck EST Project, 1995, Unpublished; GenBank Accession No. N33891, Created Jan. 11, 1996; Last Updated Jan. 11, 1996.

Hrycyna et al., "Purification and Characterization of a Novel Metalloendopeptidase from Saccharomyces Cerevisiae," Biochemistry, 1993, vol. 32, No. 42, pp. 11293–11302; GenBank Accession No. D13310.

Hirose, Direct Submission Dec. 27, 1996; GenBank Accession No. AB000170.

Sugiura et al., "Molecular Cloning of Porcine Soluble Angiotensin–binding Protein," J. Biol. Chem. 1992, vol. 267, No. 25, pp. 18067–18072; GenBank Accession No. D11336.

Hirose, Direct Submission Dec. 27, 1996; GenBank Accession No. AB000171.

Hirose, Direct Submission Dec. 27, 1996; GenBank Accession No. AB000173.

Sugiura et al., "Molecular Cloning of Porcine Soluble Angiotensin–binding Protein," J. Biol. Chem, 1992, vol. 267, No. 25, pp. 18067–18072, GenBank Accession No. Q02038.

Kawabata et al., "Rabbit Liver Microsomal Endopeptidase with Substrate Specificity for Processing Proproteins is Structurally Related to Rat Testes Metalloendopeptidase 24.15," J. Biol. Chem, 1993, vol. 268, No. 17, pp. 12498–12503; GenBank Accession No. P42675.

Hirose, Direct Submission Dec. 27, 1996; GenBank Accession No. BAA19063.

(List continued on next page.)

*Primary Examiner*—Anthony C. Caputa
*Assistant Examiner*—Gary B. Nickol
(74) *Attorney, Agent, or Firm*—Alston & Bird LLP

(57) ABSTRACT

The present invention relates to a newly identified human aminopeptidase. The invention also relates to polynucleotides encoding the aminopeptidase. The invention further relates to methods using the aminopeptidase polypeptides and polynucleotides as a target for diagnosis and treatment in aminopeptidase-related disorders. The invention further relates to drug-screening methods using the aminopeptidase polypeptides and polynucleotides to identify agonists and antagonists for diagnosis and treatment. The invention further encompasses agonists and antagonists based on the aminopeptidase polypeptides and polynucleotides. The invention further relates to procedures for producing the aminopeptidase polypeptides and polynucleotides.

14 Claims, 10 Drawing Sheets

OTHER PUBLICATIONS

Hirose, Direct Submission Dec. 27, 1996, Gen Bank Accession No. BAA19061.
Dauch et al., Direct Submission May 1995, GenBank Accession No. P42676.
Freshney (Culture of Animal Cells, A Manual of Basic Technique, Alan R. Liss, Inc., 1983, New York, p4).*
Dermer (Bio/Technology, 1994, 12:320).*
Bowie et al. (Science, 1990, 257:1306–1310).*
Burgess et al. (J of Cell Bio. 111:2129–2138, 1990).*
Lazar et al. (Molecular and Cellular Biology, 1988, 8:1247–1252).*
Bork (Genome Research, 2000, 10:398–400).*
Gura (Science v278, 1997, pp. 1041–1042).*

* cited by examiner

```
Input file 22196cons; Output File 22196tra
Sequence length 2864
TGGAAAGCTGGTACGCCTGCAGGTACCGGCGGAAAGCTGGTACGCCTGCAGGTACCGGTGGAAAGCTGGTACGCCTGCA
                                100
GGTACCGGTGGAAAGCTGGTACGCCTGCAGGTACCGGTGGAAAGCTGGTACGCCTGCAGGTACCGGTGGAAAGCTGGTA
                                200
CGCCTGCAGGTACCGGTGGAAAGCTGGTACGCCTGCAGGTACCGGTGGAAAGCTGTACGCCTGCAGGTACCGGTCCGGA
                                                                M  I  A  R        4
ATTCCCGGGTCGACCCACGCGTCCGCCCACGCGTCCGCCGCCGCCAGCCTCTCAGCGCTCCC ATG ATC GCC CGG   12   311
                                                        300
 C  L  L  A  V  R  S  L  R  R  V  G  G  S  R  I  L  L  R  M     24
TGC CTT TTG GCT GTG CGA AGC CTC CGC AGA GTT GGT GGT TCC AGG ATT TTA CTC AGA ATG   72   371
 T  L  G  R  E  V  M  S  P  L  Q  A  M  S  S  Y  T  V  A  G     44
ACG TTA GGA AGA GAA GTG ATG TCT CCT CTT CAG GCA ATG TCT TCC TAT ACC GTG GCT GGC  132   431
 R  N  V  L  R  W  D  L  S  P  E  Q  I  K  T  R  T  E  E  L     64
AGA AAT GTT TTA AGA TGG GAT CTT TCG CCA GAG CAA ATT AAA ACA AGA ACT GAG GAG CTC  192   491
 I  V  Q  T  K  Q  V  Y  D  A  V  G  M  L  G  I  E  E  V  T     84
ATT GTG CAG ACC AAG CAG GTG TAC GAT GCT GTT GGA ATG CTC GGT ATT GAG GAA GTA ACT  252   551
 Y  E  N  C  L  Q  A  L  A  D  V  E  V  K  Y  I  V  E  R  T    104
TAC GAG AAC TGT CTG CAG GCA CTG GCA GAT GTA GAA GTA AAG TAT ATA GTG GAA AGG ACC  312   611
 M  L  D  F  P  Q  H  V  S  S  D  K  E  V  R  A  A  S  T  E    124
ATG CTA GAC TTT CCC CAG CAT GTA TCC TCT GAC AAA GAA GTA CGA GCA GCA AGT ACA GAA  372   671
 A  D  K  R  L  S  R  F  D  I  E  M  S  M  R  G  D  I  F  E    144
GCA GAC AAA AGA CTT TCT CGT TTT GAT ATT GAG ATG AGC ATG AGA GGA GAT ATA TTT GAG  432   731
 R  I  V  H  L  Q  E  T  C  D  L  G  K  I  K  P  E  A  R  R    164
AGA ATT GTT CAT TTA CAG GAA ACC TGT GAT CTG GGG AAG ATA AAA CCT GAG GCC AGA CGA  492   791
 Y  L  E  K  S  I  K  M  G  K  R  N  G  L  H  L  P  E  Q  V    184
TAC TTG GAA AAG TCA ATT AAA ATG GGG AAA AGA AAT GGG CTC CAT CTT CCT GAA CAA GTA  552   851
 Q  N  E  I  K  S  M  K  K  R  M  S  E  L  C  I  D  F  N  K    204
CAG AAT GAA ATC AAA TCA ATG AAG AAA AGA ATG AGT GAG CTA TGT ATT GAT TTT AAC AAA  612   911
 N  L  N  E  D  D  T  F  L  V  F  S  K  A  E  L  G  A  L  P    224
AAC CTC AAT GAG GAT GAT ACC TTC CTT GTA TTT TCC AAG GCT GAA CTT GGT GCT CTT CCT  672   971
 D  D  F  I  D  S  L  E  K  T  D  D  D  K  Y  K  I  T  L  K    244
GAT GAT TTC ATT GAC AGT TTA GAA AAG ACA GAT GAT GAC AAG TAT AAA ATT ACC TTA AAA  732  1031
 Y  P  H  Y  F  P  V  M  K  K  C  C  I  P  E  T  R  R  R  M    264
TAT CCA CAC TAT TTC CCT GTC ATG AAG AAA TGT TGT ATC CCT GAA ACC AGA AGA AGG ATG  792  1091
 E  M  A  F  N  T  R  C  K  E  E  N  T  I  I  L  Q  Q  L  L    284
GAA ATG GCT TTT AAT ACA AGG TGC AAA GAG GAA AAC ACC ATA ATT TTG CAG CAG CTA CTC  852  1151
 P  L  R  T  K  V  A  K  L  L  G  Y  S  T  H  A  D  F  V  L    304
CCA CTG CGA ACC AAG GTG GCC AAA CTA CTC GGT TAT AGC ACA CAT GCT GAC TTC GTC CTT  912  1211
 E  M  N  T  A  K  S  T  S  R  V  T  A  F  L  D  D  L  S  Q    324
GAA ATG AAC ACT GCA AAG AGC ACA AGC CGC GTA ACA GCC TTT CTA GAT GAT TTA AGC CAG  972  1271
 K  L  K  P  L  G  E  A  E  R  E  F  I  L  N  L  K  K  K  E    344
AAG TTA AAA CCC TTG GGT GAA GCA GAA CGA GAG TTT ATT TTG AAT TTG AAG AAA AAG GAA 1032  1331
 C  K  D  R  G  F  E  Y  D  G  K  I  N  A  W  D  L  Y  Y  Y    364
TGC AAA GAC AGG GGT TTT GAA TAT GAT GGG AAA ATC AAT GCC TGG GAT CTA TAT TAC TAC 1092  1391
```

FIG. 1A.

```
  M   T   Q   T   E   E   L   K   Y   S   I   D   Q   E   F   L   K   E   Y   F      384
ATG ACT CAG ACA GAG GAA CTC AAG TAT TCC ATA GAC CAA GAG TTC CTC AAG GAA TAC TTC     1152 1451
  P   I   E   V   V   T   E   G   L   L   N   T   Y   Q   E   L   L   G   L   S      404
CCA ATT GAG GTG GTC ACT GAA GGC TTG CTG AAC ACC TAC CAG GAG TTG TTG GGA CTT TCA     1212 1511
  F   E   Q   M   T   D   A   H   V   W   N   K   S   V   T   L   Y   T   V   K      424
TTT GAA CAA ATG ACA GAT GCT CAT GTT TGG AAC AAG AGT GTT ACA CTT TAT ACT GTG AAG     1272 1571
  D   K   A   T   G   E   V   L   G   Q   F   Y   L   D   L   Y   P   R   E   G      444
GAT AAA GCT ACA GGA GAA GTA TTG GGA CAG TTC TAT TTG GAC CTC TAT CCA AGG GAA GGA     1332 1631
  K   Y   N   H   A   A   C   F   G   L   Q   P   G   C   L   L   P   D   G   S      464
AAA TAC AAT CAT GCG GCC TGC TTC GGT CTC CAG CCT GGC TGC CTT CTG CCT GAT GGA AGC     1392 1691
  R   M   M   A   V   A   A   L   V   V   N   F   S   Q   P   V   A   G   R   P      484
CGG ATG ATG GCA GTG GCT GCC CTC GTG GTG AAC TTC TCA CAG CCA GTG GCA GGT CGT CCC     1452 1751
  S   L   L   R   H   D   E   V   R   T   Y   F   H   E   F   G   H   V   M   H      504
TCT CTC CTG AGA CAC GAC GAG GTG AGG ACT TAC TTT CAT GAG TTT GGT CAC GTG ATG CAT     1512 1811
  Q   I   C   A   Q   T   D   F   A   R   F   S   G   T   N   V   E   T   D   F      524
CAG ATT TGT GCA CAG ACT GAT TTT GCA CGA TTT AGC GGA ACA AAT GTG GAA ACT GAC TTT     1572 1871
  V   E   V   P   S   Q   M   L   E   N   W   V   W   D   V   D   S   L   R   R      544
GTA GAG GTG CCA TCG CAA ATG CTT GAA AAT TGG GTG TGG GAC GTC GAT TCC CTC CGA AGA     1632 1931
  L   S   K   H   Y   K   D   G   S   P   I   A   D   D   L   L   E   K   L   V      564
TTG TCA AAA CAT TAT AAA GAT GGA AGC CCT ATT GCA GAC GAT CTG CTT GAA AAA CTT GTT     1692 1991
  A   S   R   L   V   N   T   G   L   L   T   L   R   Q   I   V   L   S   K   V      584
GCT TCT AGG CTG GTC AAC ACA GGT CTT CTG ACC CTG CGC CAG ATT GTT TTG AGC AAA GTT     1752 2051
  D   Q   S   L   H   T   N   T   S   L   D   A   A   S   E   Y   A   K   Y   C      604
GAT CAG TCT CTT CAT ACC AAC ACA TCG CTG GAT GCT GCA AGT GAA TAT GCC AAA TAC TGC     1812 2111
  S   E   I   L   G   V   A   A   T   P   G   T   N   M   P   A   T   F   G   H      624
TCA GAA ATA TTA GGA GTT GCA GCT ACT CCA GGC ACA AAT ATG CCA GCT ACC TTT GGA CAT     1872 2171
  L   A   G   G   Y   D   G   Q   Y   Y   G   Y   L   W   S   E   V   F   S   M      644
TTG GCA GGG GGA TAC GAT GGC CAA TAT TAT GGA TAT CTT TGG AGT GAA GTA TTT TCC ATG     1932 2231
  D   M   F   Y   S   C   F   K   K   E   G   I   M   N   P   E   V   G   M   K      664
GAT ATG TTT TAC AGC TGT TTT AAA AAA GAA GGG ATA ATG AAT CCA GAG GTT GGA ATG AAA     1992 2291
  Y   R   N   L   I   L   K   P   G   G   S   L   D   G   M   D   M   L   H   N      684
TAC AGA AAC CTA ATC CTG AAA CCT GGG GGA TCT CTG GAC GGC ATG GAC ATG CTC CAC AAT     2052 2351
  F   L   K   R   E   P   N   Q   K   A   F   L   M   S   R   G   L   H   A   P      704
TTC TTG AAA CGT GAG CCA AAC CAA AAA GCG TTC CTA ATG AGT AGA GGC CTG CAT GCT CCG     2112 2411
  *                                                                                   705
TGA                                                                                  2115
```

ACTGGGGATCTTTGGTAGCCGTCCATGTCTGGAGGACAAGTCGACATCACCATGTGTTACTGGCCTGGAAACTGAAGGG
AGTTTTGCAAGTGAAAATTTAGATTTCTATTGACATCCTTTTGTTTTCTAATTTTAAAAAATTATAAAGATGTAAATGGA
ATTATAAATACTGTGACCTAAGAAAAGACCCACTAGAAAGTAATTGTACTATAAAATTTCATAAAACTGGATTTGATTT
CTTTTTATGAAAGTTTCATATGAATGTAACTTGATTTTTTACTATTATAATCTAGATAATATGATATAAGAGGGCTAAA
GAATTTTAAATTGAATCATATATATGATATAATTTGATCCTTCTTGGATCTTGAAGTTTTGTACTTGGGATTCTGGAC

FIG. 1B.

TGATAATGAATCATCACATTCTTCTGGTAAATATTTTCTGGAGCTCTGTGTCAAC

FIG. 1C.

Prosite Pattern Matches for 22196

>PS00001/PDOC00001/ASN_GLYCOSYLATION N-glycosylation site.

Query: 415   NKSV   418
Query: 475   NFSQ   478
Query: 591   NTSL   594

>PS00004/PDOC00004/CAMP_PHOSPHO_SITE cAMP-and cGMP-dependent protein kinase phosphorylation site.

Query: 127   KRLS   130
Query: 193   KRMS   196
Query: 543   RRLS   546

>PS00005/PDOC00005/PKC_PHOSPHO_SITE Protein kinase C phosphorylation site.

Query: 11    SLR    13
Query: 114   SDK    116

FIG. 4A.

| Query: | 137 | SMR | 139 |
| Query: | 169 | SIK | 171 |
| Query: | 190 | SMK | 192 |
| Query: | 242 | TLK | 244 |
| Query: | 260 | TRR | 262 |
| Query: | 308 | TAK | 310 |
| Query: | 312 | TSR | 314 |
| Query: | 323 | SQK | 325 |
| Query: | 422 | TVK | 424 |
| Query: | 541 | SLR | 543 |
| Query: | 575 | TLR | 577 |

)PS00006/PDOC00006/CK2_PHOSPHO_SITE Casein kinase II phosphorylation site.

| Query: | 59 | TRTE | 62 |
| Query: | 104 | TMLD | 107 |
| Query: | 114 | SDKE | 117 |
| Query: | 123 | TEAD | 126 |
| Query: | 130 | SRFD | 133 |
| Query: | 216 | SKAE | 219 |
| Query: | 234 | TDDD | 237 |
| Query: | 298 | THAD | 301 |
| Query: | 366 | TQTE | 369 |
| Query: | 396 | TYQE | 399 |
| Query: | 422 | TVKD | 425 |
| Query: | 518 | TNVE | 521 |
| Query: | 582 | SKVD | 585 |
| Query: | 592 | TSLD | 595 |

)PS00007/PDOC00007/TYR_PHOSPHO_SITE Tyrosine kinase phosphorylation site.

| Query: | 157 | KIKPEARRY | 165 |
| Query: | 233 | KTDDDKY | 239 |
| Query: | 488 | RHDEVRTY | 495 |

)PS00008/PDOC00008/MYRISTYL N-myristoylation site.

| Query: | 392 | GLLNTY | 397 |
| Query: | 453 | GLQPGC | 458 |
| Query: | 552 | GSPIAD | 557 |
| Query: | 627 | GGYDGQ | 632 |
| Query: | 674 | GSLDGM | 679 |

)PS00009/PDOC00009/AMIDATION Amidation site.

Query: 172   MGKR   175

)PS00016/PDOC00016/RGD Cell attachment sequence.

Query: 139   RGD   141

)PS00142/PDOC00129/ZINC_PROTEASE Neutral zinc metallopeptidases, zinc-binding region signature.

Query: 494   TYFHEFGHVM   503

FIG. 4B.

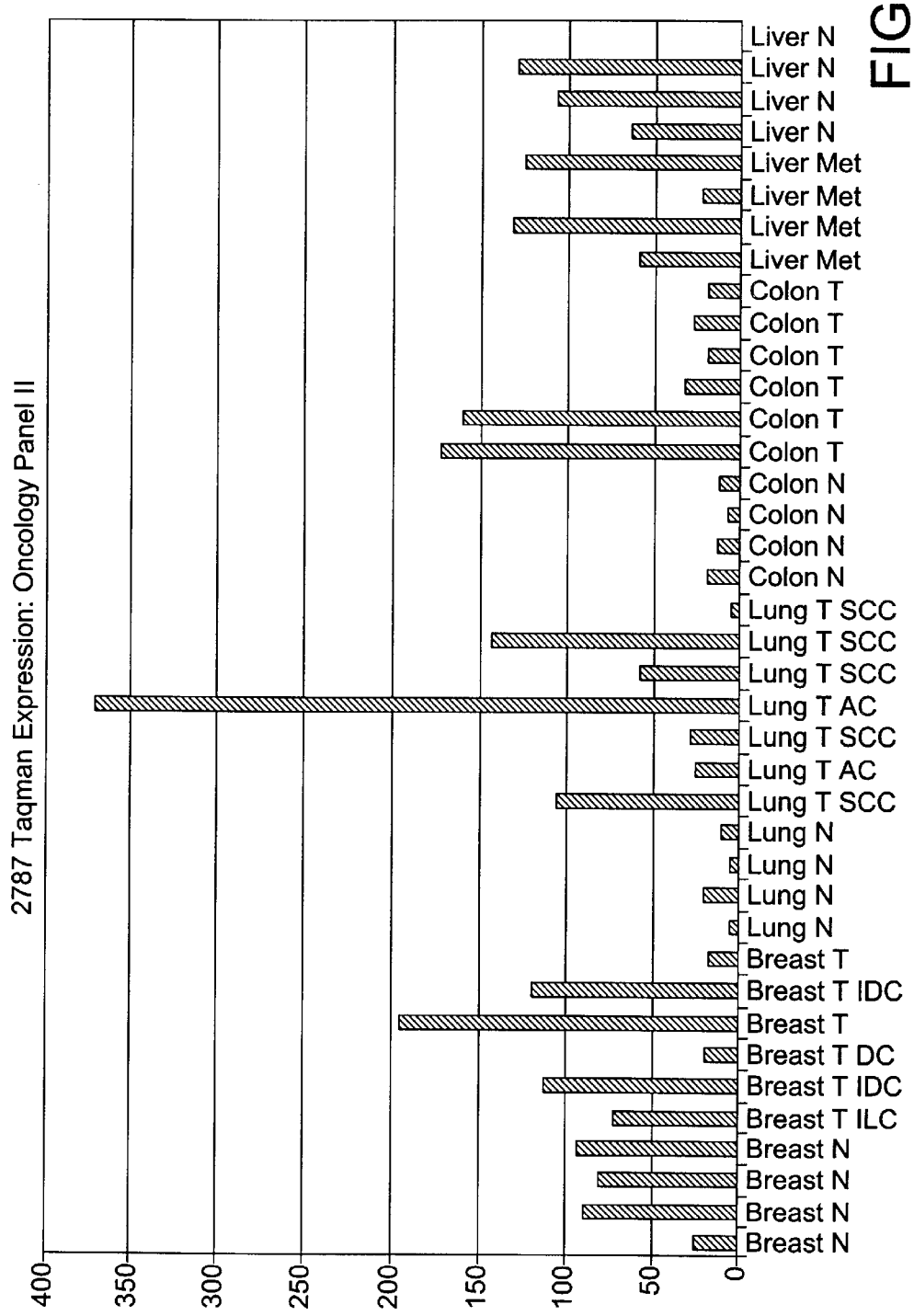

SEQUENCE LISTING

```
<160> NUMBER OF SEQ ID NOS: 3

<210> SEQ ID NO 1
<211> LENGTH: 704
<212> TYPE: PRT
<213> ORGANISM: Homo sapiens

<400> SEQUENCE: 1

Met Ile Ala Arg Cys Leu Leu Ala Val Arg Ser Leu Arg Arg Val Gly
1               5                   10                  15

Gly Ser Arg Ile Leu Leu Arg Met Thr Leu Gly Arg Glu Val Met Ser
            20                  25                  30

Pro Leu Gln Ala Met Ser Ser Tyr Thr Val Ala Gly Arg Asn Val Leu
        35                  40                  45

Arg Trp Asp Leu Ser Pro Glu Gln Ile Lys Thr Arg Thr Glu Glu Leu
    50                  55                  60

Ile Val Gln Thr Lys Gln Val Tyr Asp Ala Val Gly Met Leu Gly Ile
65                  70                  75                  80
```

```
Glu Glu Val Thr Tyr Glu Asn Cys Leu Gln Ala Leu Ala Asp Val Glu
                85                  90                  95
Val Lys Tyr Ile Val Glu Arg Thr Met Leu Asp Phe Pro Gln His Val
            100                 105                 110
Ser Ser Asp Lys Glu Val Arg Ala Ala Ser Thr Glu Ala Asp Lys Arg
        115                 120                 125
Leu Ser Arg Phe Asp Ile Glu Met Ser Met Arg Gly Asp Ile Phe Glu
    130                 135                 140
Arg Ile Val His Leu Gln Glu Thr Cys Asp Leu Gly Lys Ile Lys Pro
145                 150                 155                 160
Glu Ala Arg Arg Tyr Leu Glu Lys Ser Ile Lys Met Gly Lys Arg Asn
                165                 170                 175
Gly Leu His Leu Pro Glu Gln Val Gln Asn Glu Ile Lys Ser Met Lys
            180                 185                 190
Lys Arg Met Ser Glu Leu Cys Ile Asp Phe Asn Lys Asn Leu Asn Glu
        195                 200                 205
Asp Asp Thr Phe Leu Val Phe Ser Lys Ala Glu Leu Gly Ala Leu Pro
    210                 215                 220
Asp Asp Phe Ile Asp Ser Leu Glu Lys Thr Asp Asp Lys Tyr Lys
225                 230                 235                 240
Ile Thr Leu Lys Tyr Pro His Tyr Phe Pro Val Met Lys Lys Cys Cys
                245                 250                 255
Ile Pro Glu Thr Arg Arg Arg Met Glu Met Ala Phe Asn Thr Arg Cys
            260                 265                 270
Lys Glu Glu Asn Thr Ile Ile Leu Gln Gln Leu Leu Pro Leu Arg Thr
        275                 280                 285
Lys Val Ala Lys Leu Leu Gly Tyr Ser Thr His Ala Asp Phe Val Leu
    290                 295                 300
Glu Met Asn Thr Ala Lys Ser Thr Ser Arg Val Thr Ala Phe Leu Asp
305                 310                 315                 320
Asp Leu Ser Gln Lys Leu Lys Pro Leu Gly Glu Ala Glu Arg Glu Phe
                325                 330                 335
Ile Leu Asn Leu Lys Lys Lys Glu Cys Lys Asp Arg Gly Phe Glu Tyr
            340                 345                 350
Asp Gly Lys Ile Asn Ala Trp Asp Leu Tyr Tyr Tyr Met Thr Gln Thr
        355                 360                 365
Glu Glu Leu Lys Tyr Ser Ile Asp Gln Glu Phe Leu Lys Glu Tyr Phe
    370                 375                 380
Pro Ile Glu Val Val Thr Glu Gly Leu Leu Asn Thr Tyr Gln Glu Leu
385                 390                 395                 400
Leu Gly Leu Ser Phe Glu Gln Met Thr Asp Ala His Val Trp Asn Lys
                405                 410                 415
Ser Val Thr Leu Tyr Thr Val Lys Asp Lys Ala Thr Gly Glu Val Leu
            420                 425                 430
Gly Gln Phe Tyr Leu Asp Leu Tyr Pro Arg Glu Gly Lys Tyr Asn His
        435                 440                 445
Ala Ala Cys Phe Gly Leu Gln Pro Gly Cys Leu Leu Pro Asp Gly Ser
    450                 455                 460
Arg Met Met Ala Val Ala Ala Leu Val Val Asn Phe Ser Gln Pro Val
465                 470                 475                 480
Ala Gly Arg Pro Ser Leu Leu Arg His Asp Glu Val Arg Thr Tyr Phe
                485                 490                 495
His Glu Phe Gly His Val Met His Gln Ile Cys Ala Gln Thr Asp Phe
```

-continued

```
                500              505              510
Ala Arg Phe Ser Gly Thr Asn Val Glu Thr Asp Phe Glu Val Pro
            515                  520              525

Ser Gln Met Leu Glu Asn Trp Val Trp Asp Val Asp Ser Leu Arg Arg
    530                      535                  540

Leu Ser Lys His Tyr Lys Asp Gly Ser Pro Ile Ala Asp Asp Leu Leu
545                     550              555                 560

Glu Lys Leu Val Ala Ser Arg Leu Val Asn Thr Gly Leu Leu Thr Leu
                565             570                      575

Arg Gln Ile Val Leu Ser Lys Val Asp Gln Ser Leu His Thr Asn Thr
                580                     585             590

Ser Leu Asp Ala Ala Ser Glu Tyr Ala Lys Tyr Cys Ser Glu Ile Leu
            595             600                 605

Gly Val Ala Ala Thr Pro Gly Thr Asn Met Pro Ala Thr Phe Gly His
            610             615             620

Leu Ala Gly Gly Tyr Asp Gly Gln Tyr Tyr Gly Tyr Leu Trp Ser Glu
625             630             635                      640

Val Phe Ser Met Asp Met Phe Tyr Ser Cys Phe Lys Lys Glu Gly Ile
                645             650                  655

Met Asn Pro Glu Val Gly Met Lys Tyr Arg Asn Leu Ile Leu Lys Pro
            660             665                  670

Gly Gly Ser Leu Asp Gly Met Asp Met Leu His Asn Phe Leu Lys Arg
            675             680                  685

Glu Pro Asn Gln Lys Ala Phe Leu Met Ser Arg Gly Leu His Ala Pro
    690                 695                 700
```

```
<210> SEQ ID NO 2
<211> LENGTH: 2864
<212> TYPE: DNA
<213> ORGANISM: Homo sapiens
<220> FEATURE:
<221> NAME/KEY: CDS
<222> LOCATION: (300)...(2414)

<400> SEQUENCE: 2
tggaaagctg gtacgcctgc aggtaccggc ggaaagctgg tacgcctgca ggtaccggtg     60
gaaagctggt acgcctgcag gtaccggtgg aaagctggta cgcctgcagg taccggtgga   120
aagctggtac gcctgcaggt accggtggaa agctggtacg cctgcaggta ccggtgaaa    180 gctggtacgc ctgcaggtac cggtggaaag ctgtacgcct gcaggtaccg gtccggaatt   240
cccgggtcga cccacgcgtc cgcccacgcg tccgccgccg ccagcctctc agcgctccc    299 atg atc gcc cgg tgc ctt ttg gct gtg cga agc ctc cgc aga gtt ggt     347
Met Ile Ala Arg Cys Leu Leu Ala Val Arg Ser Leu Arg Arg Val Gly
  1               5                  10                  15 ggt tcc agg att tta ctc aga atg acg tta gga aga gaa gtg atg tct     395
Gly Ser Arg Ile Leu Leu Arg Met Thr Leu Gly Arg Glu Val Met Ser
             20                  25                  30 cct ctt cag gca atg tct tcc tat acc gtg gct ggc aga aat gtt tta     443
Pro Leu Gln Ala Met Ser Ser Tyr Thr Val Ala Gly Arg Asn Val Leu
         35                  40                  45 aga tgg gat ctt tcg cca gag caa att aaa aca aga act gag gag ctc     491
Arg Trp Asp Leu Ser Pro Glu Gln Ile Lys Thr Arg Thr Glu Glu Leu
     50                  55                  60 att gtg cag acc aag cag gtg tac gat gct gtt gga atg ctc ggt att     539
Ile Val Gln Thr Lys Gln Val Tyr Asp Ala Val Gly Met Leu Gly Ile
 65                  70                  75                  80
```

```
gag gaa gta act tac gag aac tgt ctg cag gca ctg gca gat gta gaa      587
Glu Glu Val Thr Tyr Glu Asn Cys Leu Gln Ala Leu Ala Asp Val Glu
                85                  90                  95 gta aag tat ata gtg gaa agg acc atg cta gac ttt ccc cag cat gta      635
Val Lys Tyr Ile Val Glu Arg Thr Met Leu Asp Phe Pro Gln His Val
            100                 105                 110 tcc tct gac aaa gaa gta cga gca gca agt aca gaa gca gac aaa aga      683
Ser Ser Asp Lys Glu Val Arg Ala Ala Ser Thr Glu Ala Asp Lys Arg
        115                 120                 125 ctt tct cgt ttt gat att gag atg agc atg aga gga gat ata ttt gag      731
Leu Ser Arg Phe Asp Ile Glu Met Ser Met Arg Gly Asp Ile Phe Glu
    130                 135                 140 aga att gtt cat tta cag gaa acc tgt gat ctg ggg aag ata aaa cct      779
Arg Ile Val His Leu Gln Glu Thr Cys Asp Leu Gly Lys Ile Lys Pro
145                 150                 155                 160 gag gcc aga cga tac ttg gaa aag tca att aaa atg ggg aaa aga aat      827
Glu Ala Arg Arg Tyr Leu Glu Lys Ser Ile Lys Met Gly Lys Arg Asn
                165                 170                 175 ggg ctc cat ctt cct gaa caa gta cag aat gaa atc aaa tca atg aag      875
Gly Leu His Leu Pro Glu Gln Val Gln Asn Glu Ile Lys Ser Met Lys
            180                 185                 190 aaa aga atg agt gag cta tgt att gat ttt aac aaa aac ctc aat gag      923
Lys Arg Met Ser Glu Leu Cys Ile Asp Phe Asn Lys Asn Leu Asn Glu
        195                 200                 205 gat gat acc ttc ctt gta ttt tcc aag gct gaa ctt ggt gct ctt cct      971
Asp Asp Thr Phe Leu Val Phe Ser Lys Ala Glu Leu Gly Ala Leu Pro
    210                 215                 220 gat gat ttc att gac agt tta gaa aag aca gat gat gac aag tat aaa     1019
Asp Asp Phe Ile Asp Ser Leu Glu Lys Thr Asp Asp Asp Lys Tyr Lys
225                 230                 235                 240 att acc tta aaa tat cca cac tat ttc cct gtc atg aag aaa tgt tgt     1067
Ile Thr Leu Lys Tyr Pro His Tyr Phe Pro Val Met Lys Lys Cys Cys
                245                 250                 255 atc cct gaa acc aga aga agg atg gaa atg gct ttt aat aca agg tgc     1115
Ile Pro Glu Thr Arg Arg Arg Met Glu Met Ala Phe Asn Thr Arg Cys
            260                 265                 270 aaa gag gaa aac acc ata att ttg cag cag cta ctc cca ctg cga acc     1163
Lys Glu Glu Asn Thr Ile Ile Leu Gln Gln Leu Leu Pro Leu Arg Thr
        275                 280                 285 aag gtg gcc aaa cta ctc ggt tat agc aca cat gct gac ttc gtc ctt     1211
Lys Val Ala Lys Leu Leu Gly Tyr Ser Thr His Ala Asp Phe Val Leu
    290                 295                 300 gaa atg aac act gca aag agc aca agc cgc gta aca gcc ttt cta gat     1259
Glu Met Asn Thr Ala Lys Ser Thr Ser Arg Val Thr Ala Phe Leu Asp
305                 310                 315                 320 gat tta agc cag aag tta aaa ccc ttg ggt gaa gca gaa cga gag ttt     1307
Asp Leu Ser Gln Lys Leu Lys Pro Leu Gly Glu Ala Glu Arg Glu Phe
                325                 330                 335 att ttg aat ttg aag aaa aag gaa tgc aaa gac agg ggt ttt gaa tat     1355
Ile Leu Asn Leu Lys Lys Lys Glu Cys Lys Asp Arg Gly Phe Glu Tyr
            340                 345                 350 gat ggg aaa atc aat gcc tgg gat cta tat tac tac atg act cag aca     1403
Asp Gly Lys Ile Asn Ala Trp Asp Leu Tyr Tyr Tyr Met Thr Gln Thr
        355                 360                 365 gag gaa ctc aag tat tcc ata gac caa gag ttc ctc aag gaa tac ttc     1451
Glu Glu Leu Lys Tyr Ser Ile Asp Gln Glu Phe Leu Lys Glu Tyr Phe
    370                 375                 380 cca att gag gtg gtc act gaa ggc ttg ctg aac acc tac cag gag ttg     1499
Pro Ile Glu Val Val Thr Glu Gly Leu Leu Asn Thr Tyr Gln Glu Leu
385                 390                 395                 400
```

```
ttg gga ctt tca ttt gaa caa atg aca gat gct cat gtt tgg aac aag    1547
Leu Gly Leu Ser Phe Glu Gln Met Thr Asp Ala His Val Trp Asn Lys
            405                 410                 415 agt gtt aca ctt tat act gtg aag gat aaa gct aca gga gaa gta ttg    1595
Ser Val Thr Leu Tyr Thr Val Lys Asp Lys Ala Thr Gly Glu Val Leu
        420                 425                 430 gga cag ttc tat ttg gac ctc tat cca agg gaa gga aaa tac aat cat    1643
Gly Gln Phe Tyr Leu Asp Leu Tyr Pro Arg Glu Gly Lys Tyr Asn His
            435                 440                 445 gcg gcc tgc ttc ggt ctc cag cct ggc tgc ctt ctg cct gat gga agc    1691
Ala Ala Cys Phe Gly Leu Gln Pro Gly Cys Leu Leu Pro Asp Gly Ser
        450                 455                 460 cgg atg atg gca gtg gct gcc ctc gtg gtg aac ttc tca cag cca gtg    1739
Arg Met Met Ala Val Ala Ala Leu Val Val Asn Phe Ser Gln Pro Val
465                 470                 475                 480 gca ggt cgt ccc tct ctc ctg aga cac gac gag gtg agg act tac ttt    1787
Ala Gly Arg Pro Ser Leu Leu Arg His Asp Glu Val Arg Thr Tyr Phe
            485                 490                 495 cat gag ttt ggt cac gtg atg cat cag att tgt gca cag act gat ttt    1835
His Glu Phe Gly His Val Met His Gln Ile Cys Ala Gln Thr Asp Phe
        500                 505                 510 gca cga ttt agc gga aca aat gtg gaa act gac ttt gta gag gtg cca    1883
Ala Arg Phe Ser Gly Thr Asn Val Glu Thr Asp Phe Val Glu Val Pro
            515                 520                 525 tcg caa atg ctt gaa aat tgg gtg tgg gac gtc gat tcc ctc cga aga    1931
Ser Gln Met Leu Glu Asn Trp Val Trp Asp Val Asp Ser Leu Arg Arg
        530                 535                 540 ttg tca aaa cat tat aaa gat gga agc cct att gca gac gat ctg ctt    1979
Leu Ser Lys His Tyr Lys Asp Gly Ser Pro Ile Ala Asp Asp Leu Leu
545                 550                 555                 560 gaa aaa ctt gtt gct tct agg ctg gtc aac aca ggt ctt ctg acc ctg    2027
Glu Lys Leu Val Ala Ser Arg Leu Val Asn Thr Gly Leu Leu Thr Leu
            565                 570                 575 cgc cag att gtt ttg agc aaa gtt gat cag tct ctt cat acc aac aca    2075
Arg Gln Ile Val Leu Ser Lys Val Asp Gln Ser Leu His Thr Asn Thr
        580                 585                 590 tcg ctg gat gct gca agt gaa tat gcc aaa tac tgc tca gaa ata tta    2123
Ser Leu Asp Ala Ala Ser Glu Tyr Ala Lys Tyr Cys Ser Glu Ile Leu
            595                 600                 605 gga gtt gca gct act cca ggc aca aat atg cca gct acc ttt gga cat    2171
Gly Val Ala Ala Thr Pro Gly Thr Asn Met Pro Ala Thr Phe Gly His
        610                 615                 620 ttg gca ggg gga tac gat ggc caa tat tat gga tat ctt tgg agt gaa    2219
Leu Ala Gly Gly Tyr Asp Gly Gln Tyr Tyr Gly Tyr Leu Trp Ser Glu
625                 630                 635                 640 gta ttt tcc atg gat atg ttt tac agc tgt ttt aaa aaa gaa ggg ata    2267
Val Phe Ser Met Asp Met Phe Tyr Ser Cys Phe Lys Lys Glu Gly Ile
            645                 650                 655 atg aat cca gag gtt gga atg aaa tac aga aac cta atc ctg aaa cct    2315
Met Asn Pro Glu Val Gly Met Lys Tyr Arg Asn Leu Ile Leu Lys Pro
        660                 665                 670 ggg gga tct ctg gac ggc atg gac atg ctc cac aat ttc ttg aaa cgt    2363
Gly Gly Ser Leu Asp Gly Met Asp Met Leu His Asn Phe Leu Lys Arg
            675                 680                 685 gag cca aac caa aaa gcg ttc cta atg agt aga ggc ctg cat gct ccg    2411
Glu Pro Asn Gln Lys Ala Phe Leu Met Ser Arg Gly Leu His Ala Pro
        690                 695                 700 tga actggggatc tttggtagcc gtccatgtct ggaggacaag tcgacatcac         2464
 *
```

```
catgtgttac tggcctggaa actgaaggga gttttgcaag tgaaaattta gatttctatt    2524
gacatcnttt tgttttctaa ttttaaaaat tataaagatg taaatggaat tataaatact    2584
gtgacctaag aaaagaccca ctagaaagta attgtactat aaaatttcat aaaactggat    2644
ttgatttctt tttatgaaag tttcatatga atgtaacttg atttttact attataatct     2704 agataatatg atataagagg gctaaagaat ttttaaattg aatcatatat atgatataat    2764
ttgatccttc ttggatcttg aagttttgta cttgggattc tggactgata atgaatcatc    2824
acattcttct ggtaaatatt ttctggagct ctgtgtcaac                          2864
```

<210> SEQ ID NO 3
<211> LENGTH: 6
<212> TYPE: PRT
<213> ORGANISM: Artificial Sequence
<220> FEATURE:
<223> OTHER INFORMATION: Synthetic endopeptidase substrate

<400> SEQUENCE: 3

Pro Leu Gly Pro Asp Arg
 1               5

HUMAN AMINOPEPTIDASE

FIELD OF THE INVENTION

The present invention relates to a newly identified human aminopeptidase. The invention also relates to polynucleotides encoding the aminopeptidase. The invention further relates to methods using the aminopeptidase polypeptides and polynucleotides as a target for diagnosis and treatment in aminopeptidase-related disorders. The invention further relates to drug-screening methods using the aminopeptidase polypeptides and polynucleotides to identify agonists and antagonists for diagnosis and treatment. The invention further encompasses agonists and antagonists based on the aminopeptidase polypeptides and polynucleotides. The invention further relates to procedures for producing the aminopeptidase polypeptides and polynucleotides.

BACKGROUND OF THE INVENTION

Proteases may function in carcinogenesis by inactivating or activating regulators of the cell cycle, differentiation, programmed cell death, or other processes affecting cancer development and/or progression. Consistent with the model involving protease activity and tumor progression, certain protease inhibitors have been shown to be effective inhibitors of carcinogenesis both in vitro and in vivo.

Aminopeptidases (APs) are a group of widely distributed exopeptidases that catalyse the hydrolysis of amino acid residues from the amino-terminus of polypeptides and proteins. The enzymes are found in plant and animal tissue, in eukaryotes and prokaryotes, and in secreted and soluble forms. Biological functions of aminopeptidases include protein maturation, terminal degradation of proteins, hormone level regulation, and cell-cycle control.

The enzymes are implicated in a host of conditions and disorders including aging, cancers, cataracts, cystic fibrosis and leukemias. In eukaryotes, APs are associated with removal of the initiator methionine. In prokaryotes the methionine is removed by methionine aminopeptidase subsequent to removal of the N-formyl group from the initiator N-formyl methionine, facilitating subsequent modifications such as N-acetylation and N-myristoylation. In *E. coli* AP-A (pepA), the xerB gene product is required for stabilization of unstable plasmid multimers.

APs are also involved in the metabolism of secreted regulatory molecules, such as hormones and neurotransmitters, and modulation of cell-cell interactions. In mammalian cells and tissues, the enzymes are apparently required for terminal stages of protein degradation, and EGF-induced cell-cycle control, and may have a role in protein turnover and selective elimination of obsolete or defective proteins. Furthermore, the enzymes are implicated in the supply of amino acids and energy during starvation and/or differentiation, and degradation of transported exogenous peptides to amino acids for nutrition. As leukotriene A4 hydrolase may be an aminopeptidase, APs may further have a role in inflammation. Industrial uses of the enzymes include modification of amino termini in recombinantly expressed proteins. See A. Taylor (1993) *TIBS* 18: 1993:167–172.

A variety of aminopeptidases have been identified from a wide variety of tissues and organisms, including zinc aminopeptidase and aminopeptidase M from rat kidney membrane; arginine aminopeptidase from liver; aminopeptidase $N^b$ from muscle; leucine aminopeptidase (LAP) from bovine and hog lens and kidney; aminopeptidase A (xerB gene product) from *E. coli*; yscI APE1/LAP4 and aminopeptidase A (pep4 gene product) from *S. cerevisiae*; LAP from Aeromonas; dipeptidase from mouse ascites; methionine aminopeptidase from Salmonella, *E coli, S. cerevisiae* and hog liver; and D-amino acid aminopeptidase from *Ochrobactrum anthropi* SCRC C1-38.

Of these aminopeptidases, the structure of bovine lens leucine aminopeptidase (blLAP) is well characterized and consists of a homohexamer synthesized as a large precursor, each monomer containing two thirds of the protein in a major lobe and one third in a minor lobe. The minor lobe contains the N-terminal 150 residues. All putative active site residues, presumably also the inhibitor bestatin-binding site, are found in the C-terminal lobe and include Ala-333, Asn-330, Leu360, Asp332, Asp255, Glu-334, Lys250, Asp273, Met-454, Ala-451, Gly362, Thr-359, Met270, Lys262, Gly362 and Ile-421.

Many aminopeptidases are metalloenzymes, requiring divalent cations, with specificities for $Zn^{2+}$ or $Co^{2+}$. However, particular sites of certain aminopeptidases can readily utilize $Mn^{2+}$ and $Mg^{2+}$. Residues used to ligand $Zn^{2+}$ include the His His Glu and Asp Glu Lys configurations. In addition to bestatin, boronic and phosphonic acids, α-methylleucine and isoamylthioamide are identified as competitive inhibitors for most aminopeptidases. See A. Taylor (1993) *TIBS* 18: 1993:167–172; Burley et al. (1992) *J. Mol. Biol.* 224:113–140; Taylor et al. (1993) *Biochemistry* 32:784–790.

Aminopeptidases from various organisms and various tissues within an organism have high degrees of primary sequence homology, as indicated by immunological assays. Some enzymes also exhibit very similar kinetic profiles. Direct amino acid sequence comparison of blLAP and aminopeptidase-A from *E. coli* shows 18, 44 and 35% identity for the amino- and carboxy-terminals, and the entire protein, respectively. The comparison shows 46, 66, and 60% identity for the respective regions. See Burley et al. (1992) *J. Mol. Biol.* 224:113–140.

Bovine lens leucine aminopeptidase (blLAP), bovine kidney LAP, human lens and liver LAPs, hog, lens, kidney and intestine LAPs, proline-AP, *E. coli* AP-A, AP-I and the *S. typhimurium* pepA gene product have been categorized as belonging to the family of zinc aminopeptidases which utilize the residues Asp Glu Lys for zinc binding and the active site amino acid configuration described above for bovine LAP for substrate binding. This family, possibly also including Aeromonas LAP, is suggested to be distinguished from zinc proteases which utilize His His Glu in zinc binding and Arg in substrate binding. The Saccharomyces methionine-AP is characterized to contain two zinc finger like motifs in the amino-terminus and shares little homology with blLAP. See A. Taylor (1993) *TIBS* 18: MAY 1993:167–171; Watt et al. (1989) *J. Biol. Chem.* 264:5480–5487.

Leucine aminopeptidase expression is regulated at the transcriptional level, evidenced by enhancement of both activity and mRNA upon removal of serum in in vitro aged and/or transforming lens epithelial cells. Furthermore, LAP mRNA and protein is induced by interferon γ in human ACHN renal carcinoma, A549 lung carcinoma, HS153 fibroblasts and A375 melanoma. Regulation by development and growth is also implicated. The *E. coli* pepN gene is transcriptionally regulated upon anaerobiosis and phosphate starvation. Membrane bound AP-N (CD13) is expressed in a lineage-restricted manner by subsets of normal and malignant cells, apparently through regulation by physically distinct promoters. Expression of the yeast yscI product APE1 is dependent upon the levels of yscA and PEP4 gene products. Synthesis of APE1 is sensitive to media glucose levels, and the activity of yeast aminopeptidase is sensitive to substitution of ammonia rather than peptone as the source of nitrogen. See Harris et al. (1992) *J. Biol. Chem.* 267:6865–6869; Jones et al. (1982) *Genetics* 102:665–677.

Finally, neuropeptides have long been known to affect cellular proliferation and tumor growth rates. Endopeptodases responsible for processing and degrading these neuropeptides constitute a major mechanism of control for the levels of active peptide within a given cell or tissue type. Accordingly, aminopeptidases are a major target for drug action and development. Therefore, it is valuable to the field of pharmaceutical development to identify and characterize previously unknown aminopeptidases. The present invention advances the state of the art by providing a previously unidentified human aminopeptidase.

SUMMARY OF THE INVENTION

It is an object of the invention to identify novel aminopeptidases.

It is a further object of the invention to provide novel aminopeptidase polypeptides that are usefull as reagents or targets in aminopeptidase assays applicable to treatment and diagnosis of aminopeptidase-related disorders, including but not limited to those disclosed herein.

It is a further object of the invention to provide polynucleotides corresponding to the novel aminopeptidase polypeptides that are useful as targets and reagents in aminopeptidase assays applicable to treatment and diagnosis of aminopeptidase-related disorders and useful for producing novel aminopeptidase polypeptides by recombinant methods.

A specific object of the invention is to identify compounds that act as agonists and antagonists and modulate the expression of the novel aminopeptidase.

A further specific object of the invention is to provide compounds that modulate expression of the aminopeptidase for treatment and diagnosis of aminopeptidase-related disorders.

The invention is thus based on the identification of a novel human aminopeptidase. The amino acid sequence is shown in SEQ ID NO 1. The nucleotide sequence is shown as SEQ ID NO 2.

The invention provides isolated aminopeptidase polypeptides, including a polypeptide having the amino acid sequence shown in SEQ ID NO:1 or the amino acid sequence encoded by the cDNA deposited as ATCC Patent Deposit No. PTA-1662 on Apr. 6, 2000 ("the deposited cDNA").

The invention also provides isolated aminopeptidase nucleic acid molecules having the sequence shown in SEQ ID NO 2 or in the deposited cDNA.

The invention also provides variant polypeptides having an amino acid sequence that is substantially homologous to the amino acid sequence shown in SEQ ID NO 1 or encoded by the deposited cDNA.

The invention also provides variant nucleic acid sequences that are substantially homologous to the nucleotide sequence shown in SEQ ID NO 2 or in the deposited cDNA.

The invention also provides fragments of the polypeptide shown in SEQ ID NO 1 and nucleotide sequence shown in SEQ ID NO 2, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the aminopeptidase nucleic acid molecules and polypeptides, and particularly recombinant vectors and host cells.

The invention also provides methods of making the vectors and host cells and methods for using them to produce the aminopeptidase nucleic acid molecules and polypeptides.

The invention also provides antibodies or antigen-binding fragments thereof that selectively bind the aminopeptidase polypeptides and fragments.

The invention also provides methods of screening for compounds that modulate expression or activity of the aminopeptidase polypeptides or nucleic acid (RNA or DNA).

The invention also provides a process for modulating aminopeptidase polypeptide or nucleic acid expression or activity, especially using the screened compounds. Modulation may be used to treat conditions related to aberrant activity or expression of the aminopeptidase polypeptides or nucleic acids.

The invention also provides assays for determining the activity of or the presence or absence of the aminopeptidase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the aminopeptidase nucleotide sequence (SEQ ID NO 2) and the deduced amino acid sequence (SEQ ID NO 1).

FIG. 4 shows an analysis of the aminopeptidase open reading frame for amino acids corresponding to specific functional sites of SEQ ID NO:1. Glycosylation sites are found from about amino acids 415–418, 475–478, and 591–594, with the first amino acid being the actual modified residue. Cyclic AMP and cyclic GMP dependent protein kinase phosphorylation sites are found from about amino acids 127–130, 193–196, and 543–546, with the actual modified residue being the last amino acid residue. Protein kinase C phosphorylation sites are found from about amino acids 11–13, 114–116, 137–139, 169–171, 190–192, 242–244, 260–262, 308–310, 312–314, 323–325, 422–424, 541–543 and 575–577, with the first amino acid being the actual modified residue. Casein kinase II phosphorylation sites are found from about amino acids 59–62, 104–107, 114–117, 123–126, 130–133, 216–219, 234–237, 298–301, 366–369, 396–399, 422–425, 518–521, 582–585 and 592–595, with the actual modified residue being the first amino acid. Tyrosine kinase phosphorylation sites are found from about amino acids 157–165, 233–239 and 488–495 with the last amino acid being the actual modified residue. N-myristoyolation sites are found from about amino acids 392–397, 453–458, 552–557, 627–632 and 674–679 with the first amino acid being the actual modified residue. An amidation site is found from about amino acid 172–175. The protein also contains a zinc binding region signature found in neutral zinc metallopeptidases.

FIG. 5 shows RNA expression of the aminopeptidase in normal human tissues and in carcinomas.

DETAILED DESCRIPTION OF THE INVENTION

Polypeptides

The invention is based on the identification of a novel human aminopeptidase. Specifically, an expressed sequence tag (EST) was selected based on homology to aminopeptidase sequences. This EST was used to design primers based on sequences that it contains and used to identify a cDNA from a human bone marrow cDNA library. Positive clones were sequenced and the overlapping fragments were assembled. Analysis of the assembled sequence revealed that the cloned cDNA molecule encodes an aminopeptidase.

The invention thus relates to a novel aminopeptidase having the deduced amino acid sequence shown in FIG. 1 (SEQ ID NO:1) or having the amino acid sequence encoded by the deposited cDNA, ATCC Patent Deposit No. PTA-1662.

The deposit will be maintained under the terms of the Budapest Treaty on the International Recognition of the Deposit of Microorganisms. The deposit is provided as a convenience to those of skill in the art and is not an admission that a deposit is required under 35 U.S.C. §112. The deposited sequence, as well as the polypeptides encoded by the sequence, is incorporated herein by reference and controls in the event of any conflict, such as a sequencing error, with description in this application.

"Aminopeptidase polypeptide" or "aminopeptidase protein" refers to the polypeptide in SEQ ID NO 1 or encoded by the deposited cDNA. The term "aminopeptidase protein" or "aminopeptidase polypeptide", however, further includes the numerous variants described herein, as well as fragments derived from the full-length aminopeptidase and variants.

Figure 6:
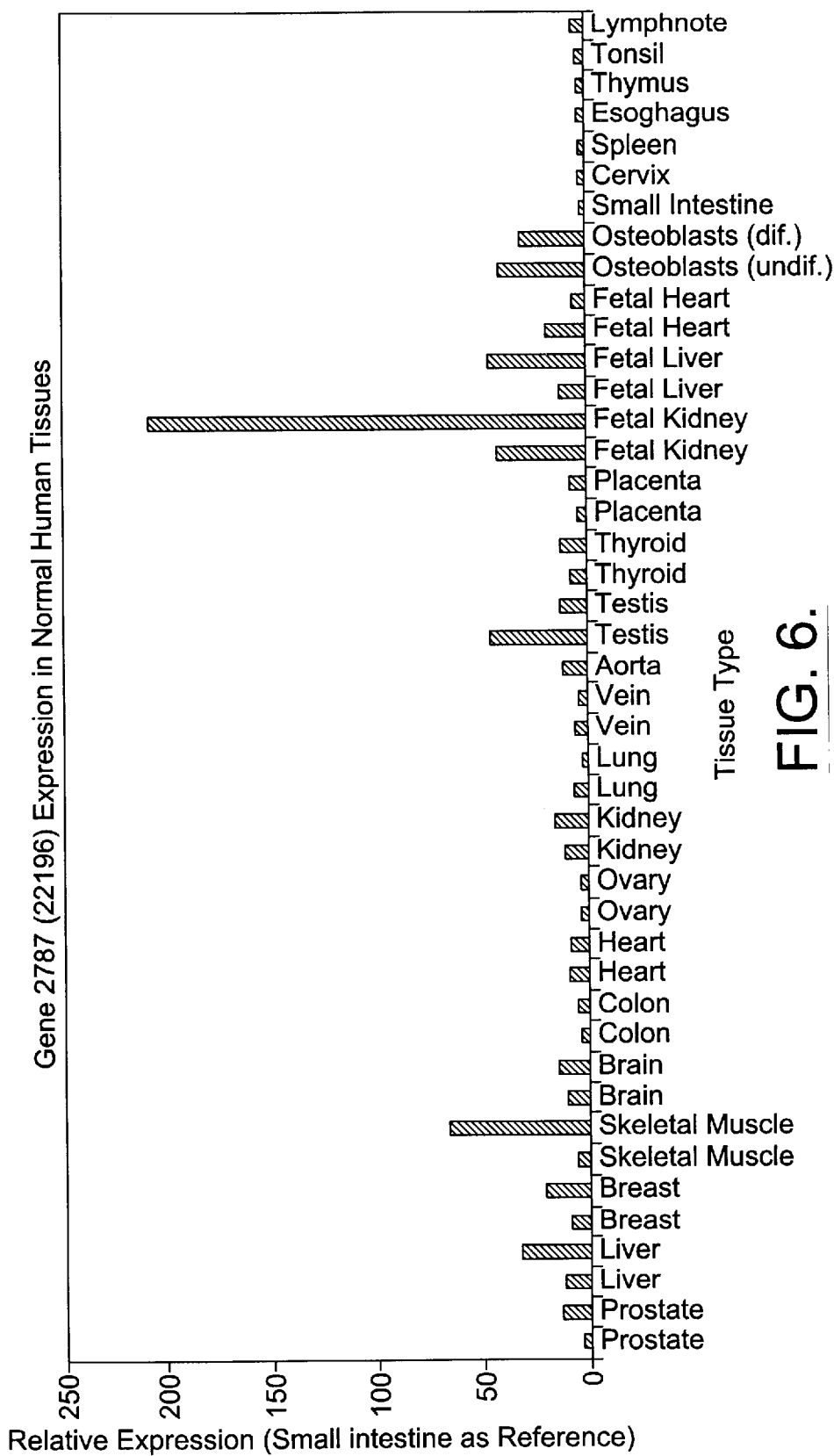
FIG. 6 shows RNA expression of the aminopeptidase in human tissues and cells.
Figure 7:
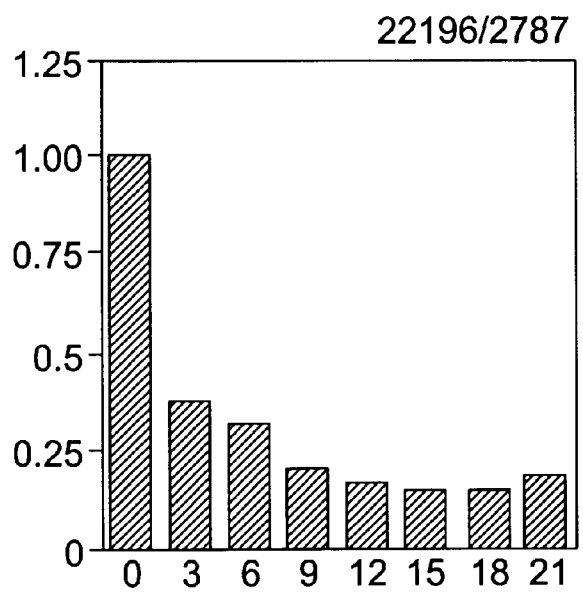
FIG. 7 shows a decrease in expression of the 22196 aminopeptidase during progression of osteoblast differentiation.

Human tissues and/or cells in which the aminopeptidase is found include, but are not limited to, those shown in FIGS. 5 and 6. The results in FIGS. 5 and 6 were obtained by Taqman expression analysis. In normal tissues, the highest expression occurred in fetal kidney, fetal liver, osteoblasts, testis and skeletal muscle. Comparison of expression in normal and tumor tissue showed that the aminopeptidase is expressed in most normal and tumor samples from breast, lung, colon and colon metastases to the liver. Pronounced increases in expression were observed in lung and colon samples. Analysis of clinical samples by RT PCR showed expression in breast, colon and lung, as well as xenograft cell lines (breast: MCF-7, ZR-75, T47D; colon: colon tumor cell lines; lung: A549, H69, H125, H322, and H460). In addition, a marked increase in repression of expression occurred during stromal cell osteoblast lineage maturation. (FIG. 7).

Taqman expression analysis was also performed in rat tissues. In normal rat tissues, the highest levels of the aminopeptidase were found in skin, followed by lung, testis, and thymus. Some expression was also observed in liver. Low levels of expression were also detected in spinal cord, dorsal root ganglia, brain, and kidney. In situ hybridization experiments showed that the aminopeptidase is expressed in a subpopulation of dorsal root ganglion neurons, in spinal cord and brain. It is also expressed in rat liver and in a subpopulation of trigeminal ganglion neurons in monkey. The aminopeptidase does not appear to be regulated in spinal cord or dorsal root ganglion neurons after 1, 3, and 7 days post-axotomy of the sciatic nerve.

The present invention thus provides an isolated or purified aminopeptidase polypeptide and variants and fragments thereof.

Based on a BLAST search, highest homology was shown to porcine neurolysin precursor (EC 3.4.24.16), Swiss Prot Accession Number q02038. This enzyme is also known as neurotensin endopeptidase, midochondral oligiopeptidase N, microsomal endopeptidase, soluble angiotensin-binding protein. See, for example, Serizawa, et al, *J. Appl. Physiol.* 270:2092–2098 (1995). Purification and characterization of this enzyme can be found in Jeohn, et al, *Eur. J. Biochem.* 260:318–324 (1999). The neuropeptide specificity and inhibition of recombinant isoforms of the endopeptidase have been studied, for example, in Rioli, et al, *Biochem. Biophys. Res. Comm.* 250:511 (1998). The enzyme has been characterized and localized in human cervical adenocarcinoma (HeLa cells). Krause, et al, *J. Cell. Biochem.* 66:297–308 (1997). Further, the effects of novel peptide inhibitors on the endopeptidase have been studied with regard to neurotension-induced analgesia and neuronal inactivitation (Vinson, et al, *Brit. J. Pharmacol.* 121:705–710 (1997)). It has also been shown that targeting of the endopeptidase to different subcellular compartments can be accomplished by alternate promoter usages (Kato, et al., *J. Biochem* 272:15313–15322(1997)). The activity and expression of soluble and membrane-associated components have been shown in stably transfected human cells over expressing this endopeptidase (Vinson, et al, *J. Neurochem.* 68:837–845 (1997)). Hydroxamate inhibitors of neurotensin degrading enzymes have also been studied, particularly with respect to synthesis and enzyme active site recognition (Bourdel, et al, *Int. J. Pep. Prot. Res.* 48:148–155 (1996)). A human endopeptidase counterpart has been purified and characterized (Vinson, et al, *J. Brain Res.* 709:51–58 (1996)). Further, neuronal and astrocytic forms of the endopeptidase have been studied with respect to differentiation, subcellular distribution, and secretion processes (Vinson, et al, *J. Neurosci.* 16:5049–5059 (1996)). Selective inhibitors of the zinc endopeptidase neurolysin have been systematically studied using combinatorial chemistry of phosphinic peptides (Jiracek, et al., *J. Biol. Chem.* 271:19606–19611 (1996)).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The aminopeptidase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the aminopeptidase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

An aminopeptidase polypeptide is also considered to be isolated when it is part of a membrane preparation or is purified and then reconstituted with membrane vesicles or liposomes.

The language "substantially free of chemical precursors or other chemicals" includes preparations of the aminopeptidase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the aminopeptidase polypeptide comprises the amino acid sequence shown in SEQ ID NO 1. However, the invention also encompasses sequence variants. Variants include a substantially homologous protein encoded by the same genetic locus in an organism, i.e., an allelic variant. Variants also encompass proteins derived from other genetic loci in an organism, but having substantial homology to the aminopeptidase of SEQ ID NO 1. Variants also include proteins substantially homologous to the aminopeptidase but derived from another organism, i.e., an ortholog. Variants also include proteins that are substantially homologous to the aminopeptidase that are produced by chemical synthesis. Variants also include proteins that are substantially homologous to the aminopeptidase that are produced by recombinant methods. It is understood, however, that variants exclude any amino acid sequences disclosed prior to the invention.

As used herein, two proteins (or a region of the proteins) are substantially homologous when the amino acid sequences are at least about 65–70%, 70–75%, 75–80%, typically at least about 80–85%, 85–90% and most typically at least about 90–95% and 95–99% or more homologous. A substantially homologous amino acid sequence, according to the present invention, will be encoded by a nucleic acid sequence hybridizing to the nucleic acid sequence, or portion thereof, of the sequence shown in SEQ ID NO 2 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 704 amino acid residues, at least 222, preferably at least 280, more preferably at least 370, even more preferably at least 440, and even more preferably at least 492, 563, 633, and 700 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the aminopeptidase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994, *Sequence Analysis in Molecular Biology*, von Heinje, G., Academic Press, 1987, and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci. USA* 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al., (1970) (*J. Mol. Biol.* 48:444–453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al., (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to the catalytic region, regulatory regions, substrate binding regions, zinc binding regions, regions involved in membrane association, and regions involved in enzyme modification, for example, by phosphorylation.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the aminopeptidase polypeptide. This includes preventing immunogenicity from pharmaceutical formulations by preventing protein aggregation.

Useful variations further include alteration of catalytic activity. For example, one embodiment involves a variation at the peptide binding site that results in binding but not hydrolysis of the peptide substrate. A further useful variation at the same site can result in altered affinity for the peptide substrate. Useful variations also include changes that provide for affinity for another peptide substrate. Another useful variation provides a fusion protein in which one or more domains or subregions are operationally fused to one or more domains or subregions from another aminopeptidase.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as peptide bond hydrolysis in vitro or related biological activity, such as proliferative activity. Assays for neurolysin activity are disclosed in the above references relating to this endopeptidase, all of which are incorporated herein by reference for their teaching regarding neurolysin activity. Examples include hydrolysis of oligopeptides, such as dynorphin A1-17, bradykinin, neurotensin, specifically at the Pro-Tyr bond, the synthetic substrate Pz (1)-Pro-Leu-Gly-Pro-D-Arg, other bioactive peptides (Barelli, et al, *Brit. J. Pharmcol.* 112:127–132 (1994); Mentlein, et al, *J. Neurochem.* 62:27–36 (1994)), inhibition by Pro-Ile, lack of thiol activitation, hydrolysis of a quenched fluorescence substrate related in structure to the Pz peptide, QF02 (Sarizawa, above), and inhibition by phosphinic peptides or other inhibitors, such as the hydroxamate inhibitors disclosed in Bourdel, et al, above. Sites that are critical for binding can also be determined by structural analysis such as crystallization, nuclear magnetic resonance or photoaffinity labeling (Smith et al. (1992) *J. Mol. Biol* 224:899–904; de Vos et al. (1992) *Science* 255:306–312).

Substantial homology can be to the entire nucleic acid or amino acid sequence or to fragments of these sequences.

The invention thus also includes polypeptide fragments of the aminopeptidase. Fragments can be derived from the amino acid sequence shown in SEQ ID NO:1. However, the invention also encompasses fragments of the variants of the aminopeptidase as described herein.

The fragments to which the invention pertains, however, are not to be construed as encompassing fragments that may be disclosed prior to the present invention.

Accordingly, a fragment can comprise at least about 10, 15, 20, 25, 30, 35, 40, 45, 50 or more contiguous amino acids. Fragments can retain one or more of the biological activities of the protein, for example the ability to bind to or hydrolyze target peptides, as well as fragments that can be used as an immunogen to generate aminopeptidase antibodies.

Biologically active fragments (peptides which are, for example, 5, 7, 10, 12, 15, 20, 30, 35, 36, 37, 38, 39, 40, 50, 100 or more amino acids in length) can comprise a functional site. Such sites include but are not limited to the catalytic site, regulatory sites, sites important for substrate recognition or binding, zinc binding region, site(s) contributing to peptide substrate specificity, phosphorylation sites, glycosylation sites, and other functional sites disclosed herein.

Such sites or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific sites or regions disclosed herein, which sub-fragments retain the function of the site or region from which they are derived.

These regions can be identified by well-known methods involving computerized homology analysis.

The invention also provides fragments with immunogenic properties. These contain an epitope-bearing portion of the aminopeptidase and variants. These epitope-bearing peptides are useful to raise antibodies that bind specifically to an aminopeptidase polypeptide or region or fragment. These peptides can contain at least 10, 12, at least 14, or between at least about 15 to about 30 amino acids.

Figure 2:
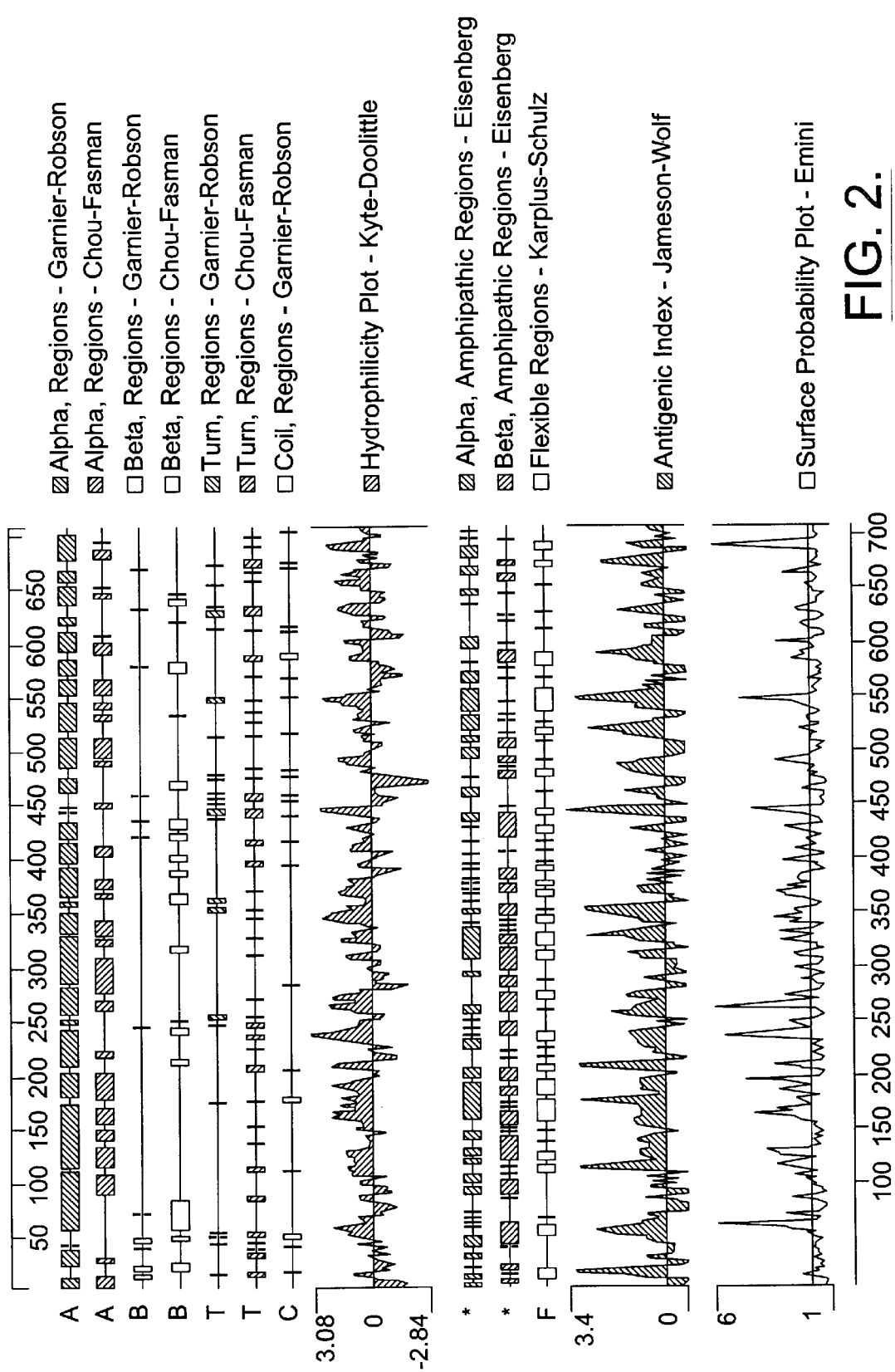
FIG. 2 shows an analysis of the aminopeptidase amino acid sequence: αβturn and coil regions; hydrophilicity; amphipathic regions; flexible regions; antigenic index; and surface probability plot.
Figure 3:
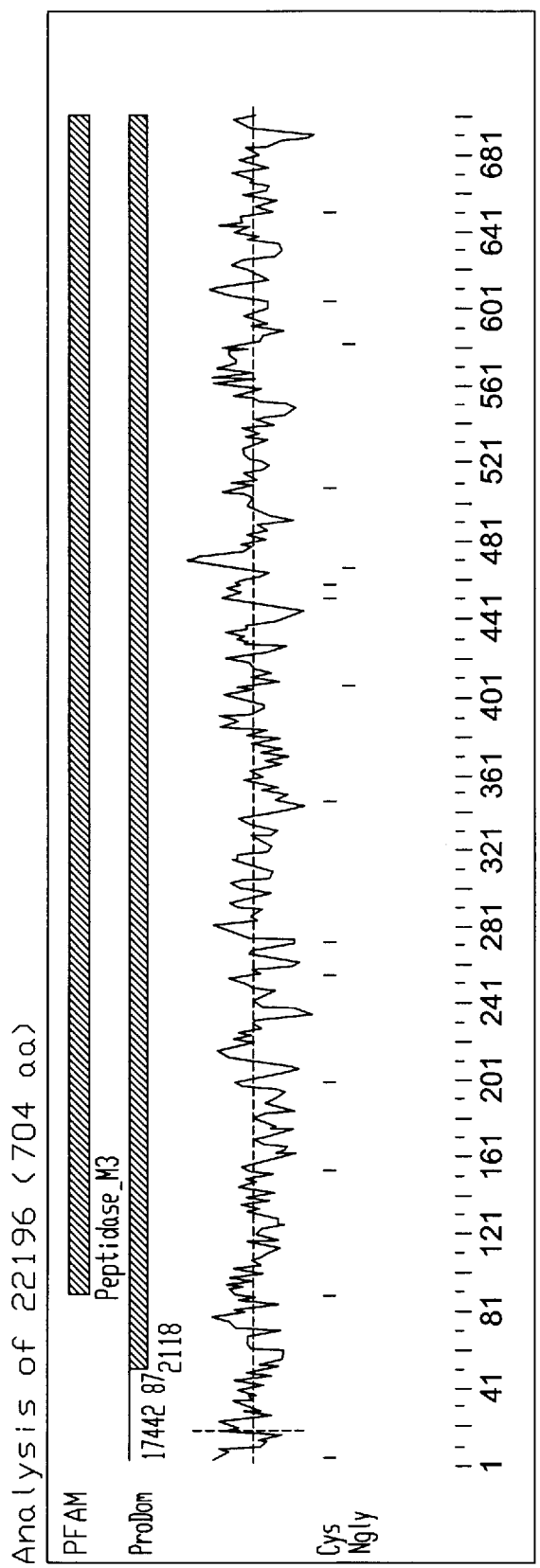
FIG. 3 shows a hydrophobicity plot of the aminopeptidase.

Non-limiting examples of antigenic polypeptides that can be used to generate antibodies include but are not limited to peptides derived from extracellular regions. Regions having a high antigenicity index are shown in FIG. 2. However, intracellularly-made antibodies ("intrabodies") are also encompassed, which would recognize intracellular peptide regions.

The epitope-bearing aminopeptidase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fised to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the aminopeptidase fragment and an additional region fused to the carboxyl terminus of the fragment.

The invention thus provides chimeric or fusion proteins. These comprise an aminopeptidase peptide sequence operatively linked to a heterologous peptide having an amino acid sequence not substantially homologous to the aminopeptidase. "Operatively linked" indicates that the aminopeptidase peptide and the heterologous peptide are fused in-frame. The heterologous peptide can be fused to the N-terminus or C-terminus of the aminopeptidase or can be internally located.

In one embodiment the fusion protein does not affect aminopeptidase function per se. For example, the fusion protein can be a GST-fusion protein in which the minopeptidase sequences are fused to the C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant aminopeptidase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing an aminopeptidase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). An aminopeptidase-encoding nucleic acid can be cloned into such an expression vector such that the fusion moiety is linked in-frame to the aminopeptidase.

Another form of fusion protein is one that directly affects aminopeptidase functions. Accordingly, an aminopeptidase polypeptide is encompassed by the present invention in which one or more of the aminopeptidase regions (or parts thereof) has been replaced by homologous regions (or parts thereof) from another aminopeptidase. Accordingly, various permutations are possible. Thus, chimeric aminopeptidases can be formed in which one or more of the native domains or subregions has been replaced by another.

Additionally, chimeric aminopeptidase proteins can be produced in which one or more functional sites is derived from a different aminopeptidase. It is understood however that sites could be derived from aminopeptidases that occur in the mammalian genome but which have not yet been discovered or characterized.

The isolated aminopeptidase protein can be purified from cells that naturally express it, such as from any of those human tissues shown in FIGS. 5 and 6. In normal tissues, the highest expression occurs in fetal kidney, fetal liver, osteoblasts, testis, and skeletal muscle. The aminopeptidase is also expressed in most normal and tumor samples from breast, lung, colon, and colon metastases to the liver. Pronounced expression is observed in lung and colon samples. Analysis of clinical samples by RT PCR shows expression in breast, colon and lung, as well as xenograft cell lines (breast: MCF-7, ZR-75, T47D, colon: colon tumor cell lines; lung: A549, H69, H125, H322, and H460). Expression also occurs in various tissues from rat as disclosed herein, especially in skin. Further, expression also occurs in monkey cells as disclosed herein. Accordingly, purification of the protein can also be accomplished using these cells. The protein can also be purified especially from cells that have been altered to express it (recombinant), or synthesized using known protein synthesis methods.

In one embodiment, the protein is produced by recombinant DNA techniques. For example, a nucleic acid molecule encoding the aminopeptidase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al., (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alingment for comparison purpose, Gapped BLAST can be utilized as described in Altschul et al., (1997) *Nucleic Acid Res.* 25(17):3389–3402. When utilizing BLAST and Gapped BLAST programs, the dafault parameters of the respective program (e.g., XBLAST and NBLAST) can be used.

The aminopeptidase polypeptides are useful for producing antibodies specific for the aminopeptidase, regions, or fragments. Regions having a high antigenicity index score are shown in FIG. 2.

The aminopeptidase polypeptides are useful for biological assays related to aminopeptidases. Such assays involve any of the aminopeptidase functions or activities or properties such as those discussed herein, useful for diagnosis and treatment of aminopeptidase-related conditions. These include disorders related to tissues in which the aminopeptidase is normally expressed, including, but not limited to, those disclosed herein, tissues in which the aminopeptidase is over-expressed, including, but not limited to, those disclosed herein, and tissues in which the aminopeptidase is otherwise inappropriate expressed, such as under-expressed or expressed in a variant form that gives rise to a pathology. These conditions are discussed in greater detail herein below.

The aminopeptidase polypeptides are also useful in drug screening assays, in cells-based or cell-free systems. Cell-based systems can be native, i.e., cells that normally express the aminopeptidase, as a biopsy or expanded in cell culture. In one embodiment, however, cell-based assays involve recombinant host cell expressing the aminopeptidase. Assays for neurolysin activity are disclosed in the above references relating to this endopeptidase, all of which are incorporated herein by reference for their teaching regarding neurolysin acitivity and assays. Examples include hydrolysis of oligopeptides, such as dynorphin A1-17, badykinin, neurotensin, specifically at the Pro-Tyr bond, the synthetic substrate Pz (1)-Pro-Leu-Gly-Pro-D-Arg(SEQ ID NO:3), other bioactive peptides (Barelli et al., *Brit. J. Pharmcol.* 112–132 (1994); Mentlein et al., *J. Neurochem.* 62:27–36 (1994), inhibition by Pro-Ile, lack of thiol activation, hydrolysis of a quenched fluorescence substrate related in structure to the Pz peptide, QF02 (Sarizawa, above), an inhibition by phosphinic peptides or other inhibitors such as the hydroxamate inhibitors discloed in Bourdel et al., above.

Determining the ability of the test compound to interact with the aminopeptidase can also comprise determining the ability of the test compound to preferentially bind to the polypeptide as compared to the ability of a known binding molecule to bind to the polyp eptide.

The polypeptides can be used to identify compounds that modulate aminopeptidase activity. Such compounds, for example, can increase or decrease affinity or rate of binding to peptide substrate, compete with peptide substrate for binding to the aminopeptidase, or displace peptide substrate bound to the aminopeptidase. Both aminopeptidase and appropriate variants and fragments can be used in high-throughput screens to assay candidate compounds for the ability to bind to the aminopeptidase. These compounds can be further screened against a functional aminopeptidase to determine the effect of the compound on the aminopeptidase activity. Compounds can be identified that activate (agonist) or inactivate (antagonist) the aminopeptidase to a desired degree. Modulatory methods can be performed in vitro (e.g., by culturing the cell with the agent) or, alternatively, in vivo (e.g., by administering the agent to a subject.

The aminopeptidase polypeptides can be used to screen a compound for the ability to stimulate or inhibit interaction between the aminopeptidase protein and a target molecule that normally interacts with the aminopeptidase protein, for example, peptide substrate or zinc component. The assay includes the steps of combining the aminopeptidase protein with a candidate compound under conditions that allow the aminopeptidase protein or fragment to interact with the target molecule, and to detect the formation of a complex between the aminopeptidase protein and the target or to detect the biochemical consequence of the interaction with the aminopeptidase and the target.

Determining the ability of the aminopeptidase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Bio.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994). *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. 409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). Candidate compounds include, but are not limited to, those discussed in the references cited herein, for example, phosphinic peptide inhibitors of neurolysin, as well as hydroxamate inhibitors of neurotensin-degrading enzymes.

One candidate compound is a soluble full-length aminopeptidase or fragment that competes for peptide binding. Other candidate compounds include mutant aminopeptidases or appropriate fragments containing mutations that affect aminopeptidase function and compete for peptide substrate. Accordingly, a fragment that competes for substrate, for example with a higher affinity, or a fragment that binds substrate but does not degrade it, is encompassed by the invention.

The invention provides other end points to identify compounds that modulate (stimulate or inhibit) aminopeptidase activity. The assays typically involve an assay of cellular events that indicate aminopeptidase activity. Thus, the expression of genes that are up- or down-regulated in response to the aminopeptidase activity can be assayed. In one embodiment, the regulatory region of such genes can be operably linked to a marker that is easily detectable, such as luciferase. Alternatively, modification of the aminopeptidase could also be measured.

Any of the biological or biochemical functions mediated by the aminopeptidase can be used as an endpoint assay. These include all of the biochemical or biochemical/biological events described herein, in the references cited herein, incorporated by reference for these endpoint assay targets, and other functions known to those of ordinary skill in the art. Specific end points can include peptide bond hydrolysis of the various substrates disclosed in the cited references and discussed herein above.

Binding and/or activating compounds can also be screened by using chimeric aminopeptidase proteins in which one or more regions, segments, sites, and the like, as disclosed herein, or parts thereof, can be replaced by their heterologous counterparts derived from other aminopeptidases. For example, a catalytic region can be used that interacts with a different peptide sequence specificity and/or affinity than the native aminopeptidase. Accordingly, a different set of components is available as an end-point assay for activation. As a further alternative, the site of modification by an effector protein, for example phosphorylation, can be replaced with the site for a different effector protein. Activation can also be detected by a reporter gene containing an easily detectable coding region operably linked to a transcriptional regulatory sequence that is part of the native pathway in which the aminopeptidase is involved.

The aminopeptidase polypeptides are also useful in competition binding assays in methods designed to discover compounds that interact with the aminopeptidase. Thus, a compound is exposed to an aminopeptidase polypeptide under conditions that allow the compound to bind or to otherwise interact with the polypeptide. Soluble aminopeptidase polypeptide is also added to the mixture. If the test compound interacts with the soluble aminopeptidase polypeptide, it decreases the amount of complex formed or activity from the aminopeptidase target. This type of assay is particularly useful in cases in which compounds are sought that interact with specific regions of the aminopeptidase. Thus, the soluble polypeptide that competes with the target aminopeptidase region is designed to contain peptide sequences corresponding to the region of interest.

Another type of competition-binding assay can be used to discover compounds that interact with specific functional sites. As an example, bindable zinc and a candidate compound can be added to a sample of the aminopeptidase. Compounds that interact with the aminopeptidase at the same site as the zinc will reduce the amount of complex formed between the aminopeptidase and the zinc. Accordingly, it is possible to discover a compound that specifically prevents interaction between the aminopeptidase and the zinc component. Another example involves adding a candidate compound to a sample of aminopeptidase and substrate peptide. A compound that competes with the peptide will reduce the amount of hydrolysis or binding of the peptide to the aminopeptidase. Accordingly, compounds can be discovered that directly interact with the aminopeptidase and compete with the peptide. Such assays can involve any other component that interacts with the aminopeptidase.

To perform cell free drug screening assays, it is desirable to immobilize either the aminopeptidase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/aminopeptidase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of aminopeptidase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an aminopeptidase-binding target component, such as a peptide or zinc component, and a candidate compound are incubated in the aminopeptidase-presenting wells and the amount of complex trapped in the well can be quantitated. Methods for detecting such complexes, in addition to those described above for the GST-immobilized complexes, include immunodetection of complexes using antibodies reactive with the aminopeptidase target molecule, or which are reactive with aminopeptidase and compete with the target molecule; as well as enzyme-linked assays which rely on detecting an enzymatic activity associated with the target molecule.

Modulators of aminopeptidase activity identified according to these drug screening assays can be used to treat a subject with a disorder related to the aminopeptidase, by treating cells that express the aminopeptidase, such as any of those shown in FIGS. 5–7 or otherwise disclosed as expressing the aminopeptidase herein. These methods of treatment include the steps of administering the modulators of aminopeptidase activity in a pharmaceutical composition as described herein, to a subject in need of such treatment.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including epatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müillerian and mesenchymal tumors, such as malignant mixed Müillerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies, toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF2) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIG. 2–8) of *Immunology, Imunopathology and Immunity*, Fifih Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms, congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma, and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts, urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas, tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angio-immunoblastic T-cell lymphoma, angiocentric lymphoma (NK/T-cell lymphoma$^{4a}$), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporois, paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, ewing saracoma, primitive neuroectodermal tumor, giant cell tumor, and metastatic tumors.

Disorders in which aminopeptidase expression is especially relevant include, but are not limited to, colon carcinoma and lung carcinoma, especially squamous cell carcinoma, and disorders related to osteoblast differentiation, especially disorders involving deficient bone mass and strength, as well as any bone disorder related to deficiency of normal bone components, for example, as discussed above.

The aminopeptidase is overexpressed in both lung and colon cancer. As such, the gene is particularly relevant for the treatment of these disorders, where modulating, especially inhibiting, expression of the gene could affect tumor development and/or progression. In addition, the fact that the gene is expressed in fetal kidney and liver to a significant degree indicates that expression of the gene is relevant to cellular proliferation, particularly in these tissues, and therefore is relevant to hyperplasia, including carconogensis, in these tissues.

Disorders that are associated with pain are relevant to expression of the 22196 gene. Since the gene is expressed in sensory ganglia (both dorsal root ganglia and trigerminal ganglia and in spinal cord, expression of the gene is relevant to the treatment of pain in disorders that are associated with painful symptoms.

The aminopeptidase polypeptides are thus useful for treating an aminopeptidase-associated disorder characterized by aberrant expression or activity of an aminopeptidase. In one embodiment, the method involves administering an agent (e.g., an agent identified by a screening assay described herein), or combination of agents that modulates (e.g., upregulates or downregulates) expression or activity of the protein. In another embodiment, the method involves administering the aminopeptidase as therapy to compensate for reduced or aberrant expression or activity of the protein.

Methods for treatment include but are not limited to the use of soluble aminopeptidase or fragments of the aminopeptidase protein that compete for substrate or any other component that directly interacts with the aminopeptidase, such as zinc or any of the enzymes that modify the aminopeptidase. These aminopeptidases or fragments can have a higher affinity for the target so as to provide effective competition. In addition, methods for treatment include substrate mimics that compete with the enzyme and thus prevent degradation of natural substrate in the case, for example, in which the endogenous enzyme is overexpressed or otherwise hyperactive.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The aminopeptidase polypeptides also are useful to provide a target for diagnosing a disease or predisposition to disease mediated by the aminopeptidase, including, but not limited to, those diseases discussed herein, and particularly lung, breast, and colon carcinoma, insulin-related disorders, such as diabetes, disorders involving aberrant osteoblast differentiation, and disorders associated with pain. Targets are useful for diagnosing a disease or predisposition to disease mediated by the aminopeptidase, such as in the tissues shown in FIGS. 5–7 and tissues in which the gene is expressed as otherwise disclosed herein. Accordingly, methods are provided for detecting the presence, or levels of, the aminopeptidase in a cell, tissue, or organism. The method involves contacting a biological sample with a compound capable of interacting with the aminopeptidase such that the interaction can be detected.

One agent for detecting aminopeptidase is an antibody capable of selectively binding to aminopeptidase. A biological sample includes tissues, cells and biological fluids isolated from a subject, as well as tissues, cells and fluids present within a subject.

The aminopeptidase also provides a target for diagnosing active disease, or predisposition to disease, in a patient having a variant aminopeptidase. Thus, aminopeptidase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered aminopeptidase activity in cell-based or cell-free assay, alteration in peptide binding or degradation, zinc binding or antibody-binding pattern, altered isoelectric point, direct amino acid sequencing, and any other of the known assay techniques useful for detecting mutations in a protein in general or in an aminopeptidase specifically.

In vitro techniques for detection of aminopeptidase include enzyme linked immunosorbent assays (ELISAs), Western blots, immunoprecipitations and immunofluorescence. Alternatively, the protein can be detected in vivo in a subject by introducing into the subject a labeled anti-aminopeptidase antibody. For example, the antibody can be labeled with a radioactive marker whose presence and location in a subject can be detected by standard imaging techniques. Particularly useful are methods, which detect the allelic variant of the aminopeptidase expressed in a subject, and methods, which detect fragments of the aminopeptidase in a sample.

The aminopeptidase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the aminopeptidase in which one or more of the aminopeptidase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The aminopeptidase polypeptides are also useful for monitoring therapeutic effects during clinical trials and other treatment. Thus, the therapeutic effectiveness of an agent that is designed to increase or decrease gene expression, protein levels or aminopeptidase activity can be monitored over the course of treatment using the aminopeptidase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the aminopeptidase and its variants and fragments. An antibody is considered to selectively bind, even if it also binds to other proteins that are not substantially homologous with the aminopeptidase. These other proteins share homology with a fragment or domain of the aminopeptidase. This conservation in specific regions gives rise to antibodies that bind to both proteins by virtue of the homologous sequence. In this case, it would be understood that antibody binding to the aminopeptidase is still selective.

To generate antibodies, an isolated aminopeptidase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 2.

Antibodies are preferably prepared from these regions or from discrete fragments in these regions. However, antibodies can be prepared from any region of the peptide as described herein. A preferred fragment produces an antibody that diminishes or completely prevents peptide hydrolysis or binding. Antibodies can be developed against the entire aminopeptidase or domains of the aminopeptidase as described herein, for example, the zinc binding region, sites contributing to peptide specificity, and the peptidase domain or subregions thereof Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate an aminopeptidase by standard techniques, such as affinity chromatography or immunoprecipitation. The antibodies can facilitate the purification of the natural aminopeptidase from cells and recombinantly produced aminopeptidase expressed in host cells.

The antibodies are useful to detect the presence of aminopeptidase in cells or tissues to determine the pattern of expression of the aminopeptidase among various tissues in an organism and over the course of normal development.

The antibodies can be used to detect aminopeptidase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length aminopeptidase can be used to identify aminopeptidase turnover.

Further, the antibodies can be used to assess aminopeptidase expression in disease states such as in active stages of the disease or in an individual with a predisposition toward disease related to aminopeptidase function. When a disorder is caused by an inappropriate tissue distribution, developmental expression, or level of expression of the aminopeptidase protein, the antibody can be prepared against the normal aminopeptidase protein. If a disorder is characterized by a specific mutation in the aminopeptidase, antibodies specific for this mutant protein can be used to assay for the presence of the specific mutant aminopeptidase. However, intracellularly-made antibodies ("intrabodies") are also encompassed, which would recognize intracellular aminopeptidase peptide regions.

The antibodies can also be used to assess normal and aberrant subcellular localization of cells in the various tissues in an organism. Antibodies can be developed against the whole aminopeptidase or portions of the aminopeptidase, for example, substrate binding and/or recognition site.

The diagnostic uses can be applied, not only in genetic testing, but also in monitoring a treatment modality. Accordingly, where treatment is ultimately aimed at correcting aminopeptidase expression level or the presence of aberrant aminopeptidases and aberrant tissue distribution or developmental expression, antibodies directed against the aminopeptidase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic aminopeptidase can be used to identify individuals that require modified treatment modalities.

The antibodies are also useful as diagnostic tools as an immunological marker for aberrant aminopeptidase analyzed by electrophoretic mobility, isoelectric point, tryptic peptide digest, and other physical assays known to those in the art.

The antibodies are also useful for tissue typing. Thus, where a specific aminopeptidase has been correlated with expression in a specific tissue, antibodies that are specific for this aminopeptidase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting aminopeptidase function, for example, zinc binding, and peptide binding and/or hydrolysis.

These uses can also be applied in a therapeutic context in which treatment involves inhibiting aminopeptidase function. An antibody can be used, for example, to block peptide binding. Antibodies can be prepared against specific fragments containing sites required for function or against intact aminopeptidase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of an aminopeptidase protein in a biological sample. The kit can comprise antibodies such as a labeled or labelable antibody and a compound or agent for detecting aminopeptidase in a biological sample; means for determining the amount of aminopeptidase in the sample; and means for comparing the amount of aminopeptidase in the sample with a standard. The compound or agent can be packaged in a suitable container. The kit can further comprise instructions for using the kit to detect aminopeptidase.

Polynucleotides

The nucleotide sequence in SEQ ID NO 2 was obtained by sequencing the deposited human cDNA. Accordingly, the sequence of the deposited clone is controlling as to any discrepancies between the two and any reference to the sequence of SEQ ID NO 2 includes reference to the sequence of the deposited cDNA.

The specifically disclosed cDNA comprises the coding region and 5' and 3' untranslated sequences in SEQ ID NO 2.

The invention provides isolated polynucleotides encoding the novel aminopeptidase. The term "aminopeptidase polynucleotide" or "aminopeptidase nucleic acid" refers to the sequence shown in SEQ ID NO 2 or in the deposited cDNA. The term "aminopeptidase polynucleotide" or "aminopeptidase nucleic acid" further includes variants and fragments of the aminopeptidase polynucleotides.

An "isolated" aminopeptidase nucleic acid is one that is separated from other nucleic acid present in the natural source of the aminopeptidase nucleic acid. Preferably, an "isolated" nucleic acid is free of sequences which naturally flank the aminopeptidase nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the aminopeptidase nucleic acid is isolated from flanking sequences such that it can be subjected to the specific manipulations described herein, such as recombinant expression, preparation of probes and primers, and other uses specific to the aminopeptidase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The aminopeptidase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The aminopeptidase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Aminopeptidase polynucleotides can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

Aminopeptidase nucleic acid can comprise the nucleotide sequences shown in SEQ ID NO 2, corresponding to human bone marrow cDNA.

In one embodiment, the aminopeptidase nucleic acid comprises only the coding region.

The invention further provides variant aminopeptidase polynucleotides, and fragments thereof, that differ from the nucleotide sequence shown in SEQ ID NO 2 due to degeneracy of the genetic code and thus encode the same protein as that encoded by the nucleotide sequence shown in SEQ ID NO 2.

The invention also provides aminopeptidase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO 2 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding an aminopeptidase that is typically at least about 60–65%, 65–70%, 70–75%, more typically at least about 80–85%, even more typically at least about 90–95%, and most typically at least about 95–99% or more homologous to the nucleotide sequence shown in SEQ ID NO 2 or a fragment of this sequence. Such nucleic acid molecules can readily be identified as being able to hybridize under stringent conditions, to the nucleotide sequence shown in SEQ ID NO 2 or a fragment of the sequence. It is understood that stringent hybridization does not indicate substantial homology where it is due to general homology, such as poly A sequences, or sequences common to all or most proteins, metalloproteases, all zinc binding proteins, all aminopeptidases, or even all neurolysins. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least 50–55%, 55% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, New York (1989), 6.3.1–6.3.6, incorporated by reference. One example of stringent hybridization conditions are hybridization in 6×sodium chloride/sodium citrate (SSC) at about 45° C., followed by one or more washes in 0.2×SSC, 0.1% SDS at 50–65° C. In another non-limiting example, nucleic acid molecules are allowed to hybridize in 6×sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO 2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO 2 or the complement of SEQ ID NO 2. In one embodiment, the nucleic acid consists of a portion of the nucleotide sequence of SEQ ID NO 2 and the complement of SEQ ID NO 2. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length aminopeptidase polynucleotides. The fragment can be single or double-stranded and can comprise DNA or RNA. The fragment can be derived from either the coding or the non-coding sequence.

In another embodiment an isolated aminopeptidase nucleic acid encodes the entire coding region. In another embodiment the isolated aminopeptidase nucleic acid encodes a sequence corresponding to the mature protein that may be from about amino acid 6 to the last amino acid. Other fragments include nucleotide sequences encoding the amino acid fragments described herein.

Thus, aminopeptidase nucleic acid fragments further include sequences corresponding to the regions described herein, subregions also described, and specific functional sites. Aminopeptidase nucleic acid fragments also include combinations of the regions, segments, motifs, and other functional sites described above. A person of ordinary skill in the art would be aware of the many permutations that are possible.

Where the location of the regions or sites have been predicted by computer analysis, one of ordinary skill would appreciate that the amino acid residues constituting these regions can vary depending on the criteria used to define the regions.

However, it is understood that an aminopeptidase fragment includes any nucleic acid sequence that does not include the entire gene.

The invention also provides aminopeptidase nucleic acid fragments that encode epitope bearing regions of the aminopeptidase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO 2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The aminopeptidase polynucleotides are thus useful for probes, primers, and in biological assays.

Where the polynucleotides are used to assess aminopeptidase properties or functions, such as in the assays described herein, all or less than all of the entire cDNA can be useful. Assays specifically directed to aminopeptidase functions, such as assessing agonist or antagonist activity, encompass the use of known fragments. Further, diagnostic methods for assessing aminopeptidase function can also be practiced with any fragment, including those fragments that may have been known prior to the invention. Similarly, in methods involving treatment of aminopeptidase dysfunction, all fragments are encompassed including those, which may have been known in the art.

The aminopeptidase polynucleotides are useful as a hybridization probe for cDNA and genomic DNA to isolate a full-length cDNA and genomic clones encoding the polypeptides described in SEQ ID NO 1 and to isolate cDNA and genomic clones that correspond to variants producing the same polypeptides shown in SEQ ID NO 1 or the other variants described herein. Variants can be isolated from the same tissue and organism from which the polypeptides shown in SEQ ID NO 1 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the aminopeptidase. Accordingly, it could be derived from 5' noncoding regions, the coding region, and 3' noncoding regions.

The nucleic acid probe can be, for example, the full-length cDNA of SEQ ID NO 2, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell aminopeptidases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol, et al, (1988) *Bio-Techniques* 6:958–976) or intercalating agents (see, e.g., Zon (1988) *Pharm Res.* 5:539–549).

The aminopeptidase polynucleotides are also useful as primers for PCR to amplify any given region of an aminopeptidase polynucleotide.

The aminopeptidase polynucleotides are also useful for constructing recombinant vectors. Such vectors include expression vectors that express a portion of, or all of, the aminopeptidase polypeptides. Vectors also include insertion vectors, used to integrate into another polynucleotide sequence, such as into the cellular genome, to alter in situ expression of aminopeptidase genes and gene products. For example, an endogenous aminopeptidase coding sequence can be replaced via homologous recombination with all or part of the coding region containing one or more specifically introduced mutations.

The aminopeptidase polynucleotides are also useful for expressing antigenic portions of the aminopeptidase proteins.

The aminopeptidase polynucleotides are also useful as probes for determining the chromosomal positions of the aminopeptidase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The aminopeptidase polynucleotide probes are also useful to determine patterns of the presence of the gene encoding the aminopeptidases and their variants with respect to tissue distribution, for example, whether gene duplication has occurred and whether the duplication occurs in all or only a subset of tissues. The genes can be naturally occurring or can have been introduced into a cell, tissue, or organism exogenously.

The aminopeptidase polynucleotides are also useful for designing ribozymes corresponding to all, or a part, of the mRNA produced from genes encoding the polynucleotides described herein.

The aminopeptidase polynucleotides are also useful for constructing host cells expressing a part, or all, of the aminopeptidase polynucleotides and polypeptides.

The aminopeptidase polynucleotides are also useful for constructing transgenic animals expressing all, or a part, of the aminopeptidase polynucleotides and polypeptides.

The aminopeptidase polynucleotides are also useful for making vectors that express part, or all, of the aminopeptidase polypeptides.

The aminopeptidase polynucleotides are also useful as hybridization probes for determining the level of aminopeptidase nucleic acid expression. Accordingly, the probes can be used to detect the presence of, or to determine levels of, aminopeptidase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the aminopeptidase genes.

Alternatively, the probe can be used in an in situ hybridization context to assess the position of extra copies of the aminopeptidase genes, as on extrachromosomal elements or as integrated into chromosomes in which the aminopeptidase gene is not normally found, for example as a homogeneously staining region.

These uses are relevant for diagnosis of disorders involving an increase or decrease in aminopeptidase expression relative to normal, such as a proliferative disorder, a differentiative or developmental disorder, or a hematopoietic disorder.

Disorders in which the aminopeptidase expression is relevant include, but are not limited to, lung and colon carcinomas and osteoblast-related disorders, especially disorders relating to aberrant osteoblast differentiation, such as disorders that result in deficient bone mass or bone strength. Disorders involving aberrant bone cell precursors are discussed herein above and hence the invention is relevant to disorders including but not limited to those disorders.

The aminopeptidase is expressed in the human tissues shown in FIGS. 5–7 and rat and monkey cells as disclosed herein. As such, the gene is particularly relevant for diagnosis of disorders involving these tissues, especially lung and colon hyperplasia and osteoblast differentiation.

Thus, the present invention provides a method for identifying a disease or disorder associated with aberrant expression or activity of aminopeptidase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the aminopeptidase, such as by measuring the level of an aminopeptidase-encoding nucleic acid in a sample of cells from a subject e.g., mRNA or genomic DNA, or determining if the aminopeptidase gene has been mutated.

Nucleic acid expression assays are useful for drug screening to identify compounds that modulate aminopeptidase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the aminopeptidase gene. The method typically includes assaying the ability of the compound to modulate the expression of the aminopeptidase nucleic acid and thus identifying a compound that can be used to treat a disorder characterized by undesired aminopeptidase nucleic acid expression.

The assays can be performed in cell-based and cell-free systems. Cell-based assays include cells naturally expressing the aminopeptidase nucleic acid or recombinant cells genetically engineered to express specific nucleic acid sequences.

Alternatively, candidate compounds can be assayed in vivo in human subjects, e.g., patients, or in transgenic animals.

The assay for aminopeptidase nucleic acid expression can involve direct assay of nucleic acid levels, such as mRNA levels, or on collateral compounds (such as peptide hydrolysis). Further, the expression of genes that are up- or down-regulated in response to the aminopeptidase activity can also be assayed. In this embodiment the regulatory regions of these genes can be operably linked to a reporter gene such as luciferase.

Thus, modulators of aminopeptidase gene expression can be identified in a method wherein a cell is contacted with a candidate compound and the expression of mRNA determined. The level of expression of aminopeptidase mRNA in the presence of the candidate compound is compared to the level of expression of aminopeptidase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate aminopeptidase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Disorders in which the aminopeptidase expression is relevant include, but are not limited to, those discussed herein, and particularly lung and colon carcinoma, osteoblast-related disorders, and disorders that are associated with painful symptoms.

Alternatively, a modulator for aminopeptidase nucleic acid expression can be a small molecule or drug identified using the screening assays described herein as long as the drug or small molecule inhibits the aminopeptidase nucleic acid expression.

The aminopeptidase polynucleotides are also useful for monitoring the effectiveness of modulating compounds on the expression or activity of the aminopeptidase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The aminopeptidase polynucleotides are also useful in diagnostic assays for qualitative changes in aminopeptidase nucleic acid, and particularly in qualitative changes that lead to pathology. The polynucleotides can be used to detect mutations in aminopeptidase genes and gene expression products such as mRNA. The polynucleotides can be used as hybridization probes to detect naturally-occurring genetic mutations in the aminopeptidase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the aminopeptidase gene associated with a dysfunction provides a diagnostic tool for an active disease or susceptibility to disease when the disease results from overexpression, underexpression, or altered expression of an aminopeptidase.

Mutations in the aminopeptidase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an aminopeptidase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant aminopeptidase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The aminopeptidase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the aminopeptidase gene that results in altered affinity for zinc could result in an excessive or decreased drug effect with standard concentrations of zinc. Accordingly, the aminopeptidase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The aminopeptidase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The aminopeptidase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the aminopeptidase sequence can be used to provide an alternative technique, which determines the actual DNA sequence of selected fragments in the genome of an individual. Thus, the aminopeptidase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The aminopeptidase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The aminopeptidase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The aminopeptidase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The aminopeptidase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of aminopeptidase probes can be used to identify tissue by species and/or by organ type.

In a similar fashion, these primers and probes can be used to screen tissue culture for contamination (i.e. screen for the presence of a mixture of different types of cells in a culture).

Alternatively, the aminopeptidase polynucleotides can be used directly to block transcription or translation of aminopeptidase gene sequences by means of antisense or ribozyme constructs. Thus, in a disorder characterized by abnormally high or undesirable aminopeptidase gene expression, nucleic acids can be directly used for treatment.

The aminopeptidase polynucleotides are thus useful as antisense constructs to control aminopeptidase gene expression in cells, tissues, and organisms. A DNA antisense polynucleotide is designed to be complementary to a region of the gene involved in transcription, preventing transcription and hence production of aminopeptidase protein. An antisense RNA or DNA polynucleotide would hybridize to the mRNA and thus block translation of mRNA into aminopeptidase protein.

Examples of antisense molecules useful to inhibit nucleic acid expression include antisense molecules complementary to a fragment of the 5' untranslated region of SEQ ID NO 2 which also includes the start codon and antisense molecules which are complementary to a fragment of the 3' untranslated region of SEQ ID NO 2.

Alternatively, a class of antisense molecules can be used to inactivate mRNA in order to decrease expression of aminopeptidase nucleic acid. Accordingly, these molecules can treat a disorder characterized by abnormal or undesired aminopeptidase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the aminopeptidase protein.

The aminopeptidase polynucleotides also provide vectors for gene therapy in patients containing cells that are aberrant in aminopeptidase gene expression. Thus, recombinant cells, which include the patient's cells that have been engineered ex vivo and returned to the patient, are introduced into an individual where the cells produce the desired aminopeptidase protein to treat the individual.

The invention also encompasses kits for detecting the presence of an aminopeptidase nucleic acid in a biological sample. For example, the kit can comprise reagents such as a labeled or labelable nucleic acid or agent capable of detecting aminopeptidase nucleic acid in a biological sample; means for determining the amount of aminopeptidase nucleic acid in the sample; and means for comparing the amount of aminopeptidase nucleic acid in the sample with a standard. The compound or agent can be packaged in a suitable container. The kit can further comprise instructions for using the kit to detect aminopeptidase mRNA or DNA.

Computer Readable Means

The nucleotide or amino acid sequences of the invention are also provided in a variety of mediums to facilitate use thereof As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM, electrical storage media such as RAM and ROM, and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the aminopeptidase polynucleotides. The term "vector" refers to a vehicle, preferably a nucleic acid molecule that can transport the aminopeptidase polynucleotides. When the vector is a nucleic acid molecule, the aminopeptidase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the aminopeptidase polynucleotides. Alternatively, the vector may integrate into the host cell genome and produce additional copies of the aminopeptidase polynucleotides when the host cell replicates.

The invention provides vectors for the maintenance (cloning vectors) or vectors for expression (expression vectors) of the aminopeptidase polynucleotides. The vectors can function in procaryotic or eukaryotic cells or in both (shuttle vectors).

Expression vectors contain cis-acting regulatory regions that are operably linked in the vector to the aminopeptidase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the aminopeptidase polynucleotides from the vector. Alternatively, a trans-acting factor may be supplied by the host cell. Finally, a trans-acting factor can be produced from the vector itself It is understood, however, that in some embodiments, transcription and/or translation of the aminopeptidase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. Coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd.* ed, Cold Spring Harbor Laboratory Press, Cold Spring Harbor, N.Y.).

A variety of expression vectors can be used to express an aminopeptidase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd.* ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The aminopeptidase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the aminopeptidase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety.

Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The aminopeptidase polynucleotides can also be expressed by expression vectors that are operative in yeast. Examples of vectors for expression in yeast e.g., *S. cerevisiae* include pYepSe1 (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The aminopeptidase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the aminopeptidase polynucleotides. The person of ordinary skill in the art would be aware of other vectors suitable for maintenance propagation or expression of the polynucleotides described herein. These are found for example in Sambrook et al. (1989) *Molecular Cloning. A Laboratory Manual 2nd.*, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning. A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the aminopeptidase polynucleotides can be introduced either alone or with other polynucleotides that are not related to the aminopeptidase polynucleotides such as those providing trans-acting factors for expression vectors. When more than one vector is introduced into a cell, the vectors can be introduced independently, co-introduced or joined to the aminopeptidase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the aminopeptidase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing aminopeptidase proteins or polypeptides that can be further purified to produce desired amounts of aminopeptidase protein or fragments. Thus, host cells containing expression vectors are useful for polypeptide production.

Host cells are also useful for conducting cell-based assays involving the aminopeptidase or aminopeptidase fragments. Thus, a recombinant host cell expressing a native aminopeptidase is useful to assay for compounds that stimulate or inhibit aminopeptidase function. This includes zinc or peptide binding, gene expression at the level of transcription or translation, and interaction with other cellular components.

Host cells are also useful for identifying aminopeptidase mutants in which these functions are affected. If the mutants naturally occur and give rise to a pathology, host cells containing the mutations are useful to assay compounds that have a desired effect on the mutant aminopeptidase (for example, stimulating or inhibiting function) which may not be indicated by their effect on the native aminopeptidase.

Recombinant host cells are also useful for expressing the chimeric polypeptides described herein to assess compounds that activate or suppress activation by means of a heterologous domain, segment, site, and the like, as disclosed herein.

Further, mutant aminopeptidases can be designed in which one or more of the various functions is engineered to be increased or decreased and used to augment or replace aminopeptidase proteins in an individual. Thus, host cells can provide a therapeutic benefit by replacing an aberrant aminopeptidase or providing an aberrant aminopeptidase that provides a therapeutic result. In one embodiment, the cells provide aminopeptidases that are abnormally active.

In another embodiment, the cells provide aminopeptidases that are abnormally inactive. These aminopeptidases can compete with endogenous aminopeptidases in the individual.

In another embodiment, cells expressing aminopeptidases that cannot be activated, are introduced into an individual in order to compete with endogenous aminopeptidases for zinc or peptide. For example, in the case in which excessive zinc is part of a treatment modality, it may be necessary to effectively inactivate zinc at a specific point in treatment. Providing cells that compete for the molecule, but which cannot be affected by aminopeptidase activation would be beneficial.

Homologously recombinant host cells can also be produced that allow the in situ alteration of endogenous aminopeptidase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. No. 5,272,071, and U.S. Pat No. 5,641,670. Briefly, specific polynucleotide sequences corresponding to the aminopeptidase polynucleotides or sequences proximal or distal to an aminopeptidase gene are allowed to integrate into a host cell genome by homologous recombination where expression of the gene can be affected. In one embodiment, regulatory sequences are introduced that either increase or decrease expression of an endogenous sequence. Accordingly, an aminopeptidase protein can be produced in a cell not normally producing it. Alternatively, increased expression of aminopeptidase protein can be effected in a cell normally producing the protein at a specific level. Further, expression can be decreased or eliminated by introducing a specific regulatory sequence. The regulatory sequence can be heterologous to the aminopeptidase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant aminopeptidase proteins. Such mutations could be introduced, for example, into the specific functional regions such as the substrate-binding site.

In one embodiment, the host cell can be a fertilized oocyte or embryonic stem cell that can be used to produce a transgenic animal containing the altered aminopeptidase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous aminopeptidase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an aminopeptidase protein and identifying and evaluating modulators of aminopeptidase protein activity.

Other examples of transgenic animals include non-human primates, sheep, dogs, cows, goats, chickens, and amphibians.

In one embodiment, a host cell is a fertilized oocyte or an embryonic stem cell into which aminopeptidase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal.

Any of the aminopeptidase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the aminopeptidase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding or activation, may not be evident from in vitro cell-free or cell-based assays. Accordingly, it is useful to provide non-human transgenic animals to assay in vivo aminopeptidase function, including peptide interaction, the effect of specific mutant aminopeptidases on aminopeptidase function and peptide interaction, and the effect of chimeric aminopeptidases. It is also possible to assess the effect of null mutations, that is mutations that substantially or completely eliminate one or more aminopeptidase functions.

In general, methods for producing transgenic animals include introducing a nucleic acid sequence according to the present invention, the nucleic acid sequence capable of expressing the receptor protein in a transgenic animal, into a cell in culture or in vivo. When introduced in vivo, the nucleic acid is introduced into an intact organism such that one or more cell types and, accordingly, one or more tissue types, express the nucleic acid encoding the receptor protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions

The aminopeptidase nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo by in vivo transcription or translation of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an aminopeptidase protein or anti-aminopeptidase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. An isolated nucleic acid molecule having a nucleotide sequence selected from the group consisting of:
   (a) the nucleotide sequence shown in SEQ ID NO:2;
   (b) the nucleotide sequence of the cDNA insert contained in ATCC Patent Deposit No. PTA-1662; and
   (c) a nucleotide sequence exactly complementary to any of the nucleotide sequences in (a) or (b).

2. A nucleic acid vector comprising the nucleic acid sequences in claim 1.

3. A host cell containing the vector of claim 2.

4. A kit comprising reagents for use in a method for detecting the presence of a nucleotide sequence selected from the group consisting of:
   (a) the nucleotide sequence set forth in SEQ ID NO:2;
   (b) the nucleotide sequence in the cDNA insert contained in ATCC Patent Deposit No. PTA-1662;
   (c) a nucleotide sequence encoding the amino acid sequence set forth in SEQ ID NO:1;
   (d) a nucleotide sequence encoding the amino acid sequence encoded by the cDNA insert contained in ATCC Patent Deposit No. PTA-1662; and
   (e) a nucleotide sequence exactly complementary to any of the nucleotide sequences in (a), (b), (c), or (d);
in a sample, the method comprising contacting the sample with a nucleic acid probe that hybridizes to the nucleotide sequence under stringent conditions and determining whether the nucleic acid probe binds to the nucleotide sequence in the sample, wherein said stringent conditions comprise hybridization in 6×SSC at about 45° C. followed by one or more washes in 0.2×SSC/0.1% SDS at 65° C. and the reagents comprise the nucleic acid probe wherein said probe consists of at least 12 nucleotides of SEQ ID NO:2.

5. The kit of claim 4, wherein a fragment of the nucleotide sequence is contacted.

6. A composition containing any of the nucleic acid molecules of claim 1 in a pharmaceutically-acceptable carrier.

7. An isolated nucleic acid molecule having a nucleotide sequence selected from the group consisting of:
   (a) a nucleotide sequence encoding the amino acid sequence shown in SEQ ID NO:1;
   (b) a nucleotide sequence encoding the amino acid sequence encoded by the cDNA insert of the plasmid contained in ATCC Patent Deposit No. PTA-1662; and
   (c) a nucleotide sequence exactly complementary to any of the nucleotide sequences in (a) or (b).

8. A nucleic acid vector comprising the nucleic acid molecule of claim 7.

9. A host cell containing the vector of claim 8.

10. An isolated nucleic acid molecule having a nucleotide sequence selected from the group consisting of:
    (a) a nucleotide sequence encoding a fragment of the amino acid sequence shown in SEQ ID NO:1, wherein said fragment comprises at least 100 contiguous amino acids of the amino acid sequence shown in SEQ ID NO:1; and
    (b) a nucleotide sequence exactly complementary to a nucleotide sequence of (a).

11. A nucleic acid vector comprising the nucleic acid molecule of claim 10.

12. A host cell containing the vector of claim 11.

13. A method for producing a polypeptide encoded by a nucleic acid molecule comprising a nucleotide sequence selected from the group consisting of:
    (a) the nucleotide sequence shown in SEQ ID NO:2;
    (b) the nucleotide sequence of the cDNA insert contained in ATCC Patent Deposit No. PTA-1662;
    (c) a nucleotide sequence encoding the amino acid sequence shown in SEQ ID NO:1; and
    (d) a nucleotide sequence encoding the amino acid sequence encoded by the cDNA insert of the plasmid contained in ATCC Patent Deposit No. PTA-1662;
said method comprising introducing the nucleic acid molecule into a host cell and culturing the host cell under conditions in which the polypeptide is expressed from the nucleic acid molecule.

14. A method for producing a polypeptide encoded by a nucleic acid molecule comprising a nucleotide sequence selected from the group consisting of:

(a) a nucleotide sequence encoding a fragment of the amino acid sequence shown in SEQ ID NO:1, wherein the fragment comprises at least 100 contiguous amino acids of the amino acid sequence shown in SEQ ID NO:1;

(b) a nucleotide sequence encoding a fragment of the amino acid sequence encoded by the cDNA insert of the plasmid deposited as ATCC Patent Deposit No. PTA-1662, wherein the fragment comprises at least 100 contiguous amino acids of the amino acid sequence encoded by the cDNA insert of the plasmid deposited as ATCC Pat. Deposit No. PTA-1662;

(c) a nucleotide sequence encoding the amino acid sequence of the mature polypeptide set forth from amino acid 6 to the last amino acid shown in SEQ ID NO:1; and (d) a nucleotide sequence encoding the amino acid sequence of the mature polypeptide from amino acid 6 to the last amino acid encoded by the cDNA insert deposited with ATCC as Patent Deposit No. PTA-1662;

said method comprising introducing the nucleic acid molecule into a host cell, and culturing the host cell under conditions in which the polypeptide is expressed from the nucleic acid molecule.

* * * * *

UNITED STATES PATENT AND TRADEMARK OFFICE
CERTIFICATE OF CORRECTION

PATENT NO.    : 6,444,802 B1
DATED         : September 3, 2002
INVENTOR(S)   : Kapeller-Libermann et al.

It is certified that error appears in the above-identified patent and that said Letters Patent is hereby corrected as shown below:

<u>Title page,</u>
Item [75], Inventors, the third name "Immaculada" should read -- Inmaculada --.
Item [73], Assignee, "Millenium" should read -- Millennium --.

Signed and Sealed this

Eleventh Day of March, 2003

JAMES E. ROGAN
*Director of the United States Patent and Trademark Office*